United States Patent
Breitweiser et al.

(10) Patent No.: US 12,008,671 B2
(45) Date of Patent: Jun. 11, 2024

(54) POLICYHOLDER SETUP IN SECURE PERSONAL AND FINANCIAL INFORMATION STORAGE AND CHATBOT ACCESS BY TRUSTED INDIVIDUALS

(71) Applicant: STATE FARM MUTUAL AUTOMOBILE INSURANCE COMPANY, Bloomington, IL (US)

(72) Inventors: Edward W. Breitweiser, Bloomington, IL (US); Brian A. Steigerwald, Bloomington, IL (US); Shreeti Banerjee, Bloomington, IL (US); Larry Ingrum, Mahomet, IL (US)

(73) Assignee: State Farm Mutual Automobile Insurance Company, Bloomington, IL (US)

( * ) Notice: Subject to any disclaimer, the term of this patent is extended or adjusted under 35 U.S.C. 154(b) by 0 days.

(21) Appl. No.: 18/074,555

(22) Filed: Dec. 5, 2022

(65) Prior Publication Data
US 2023/0105564 A1    Apr. 6, 2023

Related U.S. Application Data

(63) Continuation of application No. 17/089,388, filed on Nov. 4, 2020, now Pat. No. 11,544,807.
(Continued)

(51) Int. Cl.
*G06Q 50/18* (2012.01)
*G06Q 40/08* (2012.01)
(Continued)

(52) U.S. Cl.
CPC .......... *G06Q 50/186* (2013.01); *G06Q 40/08* (2013.01); *H04L 51/02* (2013.01); *H04L 51/04* (2013.01)

(58) Field of Classification Search
CPC ...... G06Q 50/186; G06Q 40/08; H04L 51/02; H04L 51/04
See application file for complete search history.

(56) References Cited

U.S. PATENT DOCUMENTS 5,946,657 A    8/1999    Svevad
9,892,463 B1    2/2018    Hakimi et al.
(Continued)

FOREIGN PATENT DOCUMENTS

WO    2016/050990 A1    4/2016

OTHER PUBLICATIONS

Adrienne Matei, New technology is forcing us to confront the ethics of bringing people back from the dead, Jan. 27, 2017, Quartz Ideas, https://qz.com/896207/death-technology-will-allow-grieving-people-to-bring-back-their-loved ones-from-the-dead-digitally/, Jul. 10, 2018.
(Continued)

*Primary Examiner* — Suraj M Joshi
(74) *Attorney, Agent, or Firm* — Lee & Hayes, P.C.

(57) ABSTRACT

A computer-implement method and computer system may be configured to facilitate policyholder setup in connection with estate handling. An audible or visible chatbot avatar or doppleganger may lead a trustee, beneficiary, or family member through the estate of an impaired or deceased user. A computer system may have been provided with, or gather, sample voice and visual recordings associated with a user that are used to build the chatbot avatar that simulates the user audibly and/or visually. The computer system may have previously prompted the user for necessary items to properly handle their estate, such as information related to financial accounts, loans, insurance policies, etc. and user names and passwords to various electronic accounts.

18 Claims, 11 Drawing Sheets

Related U.S. Application Data

(60) Provisional application No. 63/108,528, filed on Nov. 2, 2020, provisional application No. 62/947,374, filed on Dec. 12, 2019, provisional application No. 62/931,486, filed on Nov. 6, 2019, provisional application No. 62/930,830, filed on Nov. 5, 2019.

(51) Int. Cl.
 H04L 51/02 (2022.01)
 H04L 51/04 (2022.01)

(56) References Cited

U.S. PATENT DOCUMENTS

| | | | |
|---|---|---|---|
| 10,055,793 | B1 | 8/2018 | Call et al. |
| 10,066,793 | B2 | 9/2018 | Cornelissen |
| 10,068,228 | B1 | 9/2018 | Winklevoss et al. |
| 10,937,104 | B1 | 3/2021 | Fiedler et al. |
| 2009/0171828 | A1 | 7/2009 | Molinsky et al. |
| 2010/0241465 | A1 | 9/2010 | Amigo et al. |
| 2011/0313794 | A1 | 12/2011 | Feeney |
| 2012/0303390 | A1 | 11/2012 | Brook et al. |
| 2013/0035965 | A1 | 2/2013 | Wood |
| 2013/0124229 | A1 | 5/2013 | Cashman et al. |
| 2013/0290198 | A1 | 10/2013 | Vassil |
| 2015/0019311 | A1* | 1/2015 | Lee ............... G06Q 30/0214 |
| | | | 705/14.16 |
| 2015/0073907 | A1 | 3/2015 | Purves et al. |
| 2015/0254795 | A1 | 9/2015 | Levin et al. |
| 2016/0070777 | A1* | 3/2016 | Lubeck .............. G06F 16/9535 |
| | | | 707/740 |
| 2017/0300643 | A1 | 10/2017 | Bezark et al. |
| 2017/0364637 | A1* | 12/2017 | Kshepakaran ........ G16H 10/60 |
| 2018/0082391 | A1 | 3/2018 | Brody |
| 2018/0173999 | A1 | 6/2018 | Renard |
| 2019/0179913 | A1* | 6/2019 | Osthus ................. G06F 16/248 |
| 2019/0304012 | A1 | 10/2019 | Ramirez et al. |
| 2020/0066391 | A1 | 2/2020 | Sachdeva et al. |
| 2020/0311625 | A1 | 10/2020 | Bender et al. |
| 2021/0407504 | A1* | 12/2021 | Colleen ................... G06N 5/02 |

OTHER PUBLICATIONS

Fussell, S. (2016). You can create an online avatar that lives on after you die-but what's the point Splinter. httpssplinternews.comyou-can-create-an-online-avatar-that-lives-on-after-you-1793862007. (Year: 2016).

Sally Abrahms, 3 Great Web Sites for Organizing Estate-Planning Documents, Nov. 1, 2015, Kiplinger's Retirement Report, Nov. 2015, https://www.kiplinger.com/article/retirement/t021-c000-s004-all-documents-in-one-place-online.html, Jul. 10, 2018.

Shriya, Devadiga, and Bhakthi Shetty. "Resurrection of Digital Consciousness Using Artificial Intelligence." Asian Journal for Convergence in Technology (AJCT) ISSN-2350-1146 (2018). (Year: 2018).

The chatbot that lets you talk to the dead, Oct. 11, 2016, the Guardian, https://www.theguardian.com/technology/shortcuts/2016/oct/11/chatbot-talk-to-dead-grief, Jul. 10, 2018.

* cited by examiner

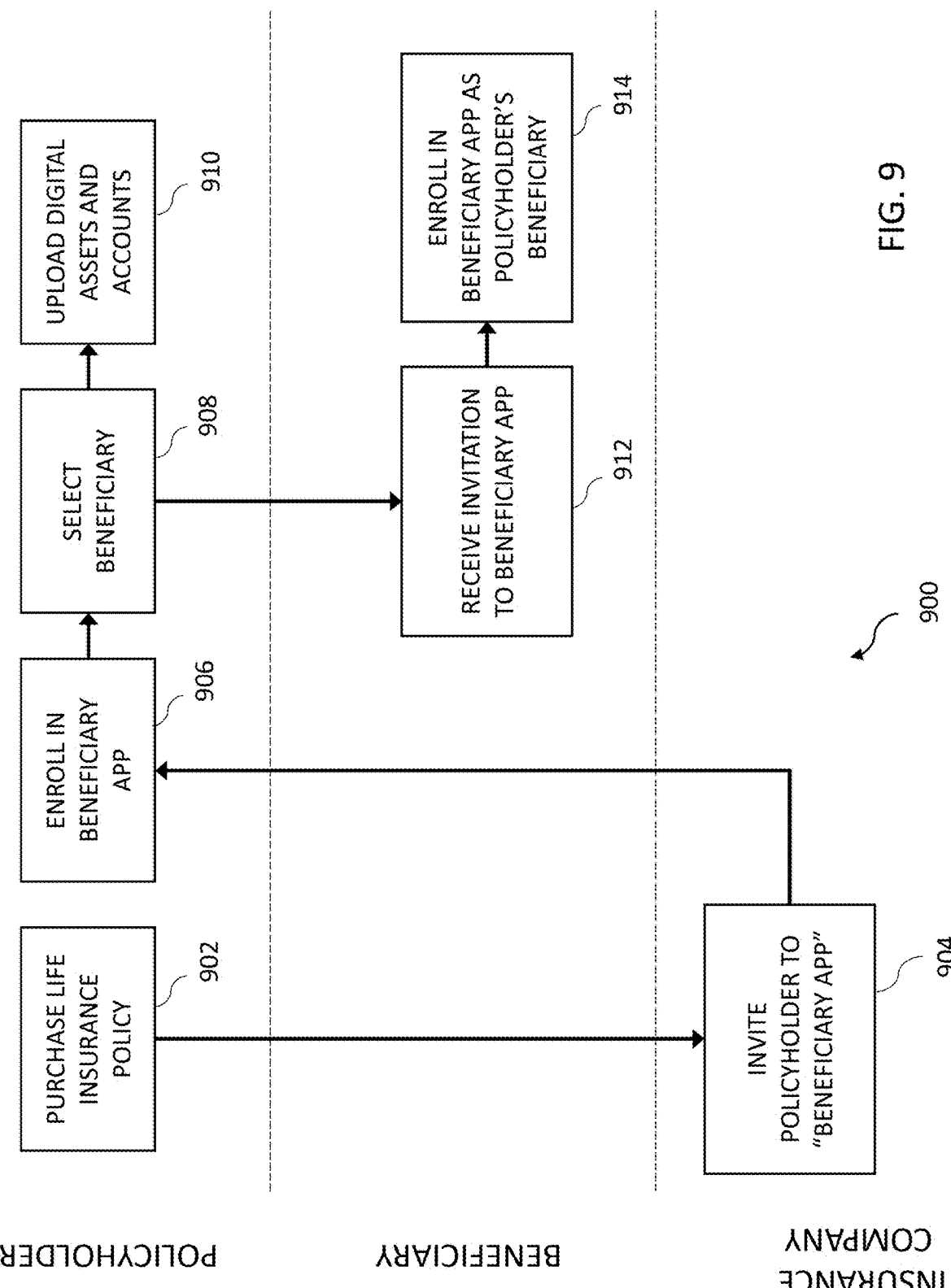

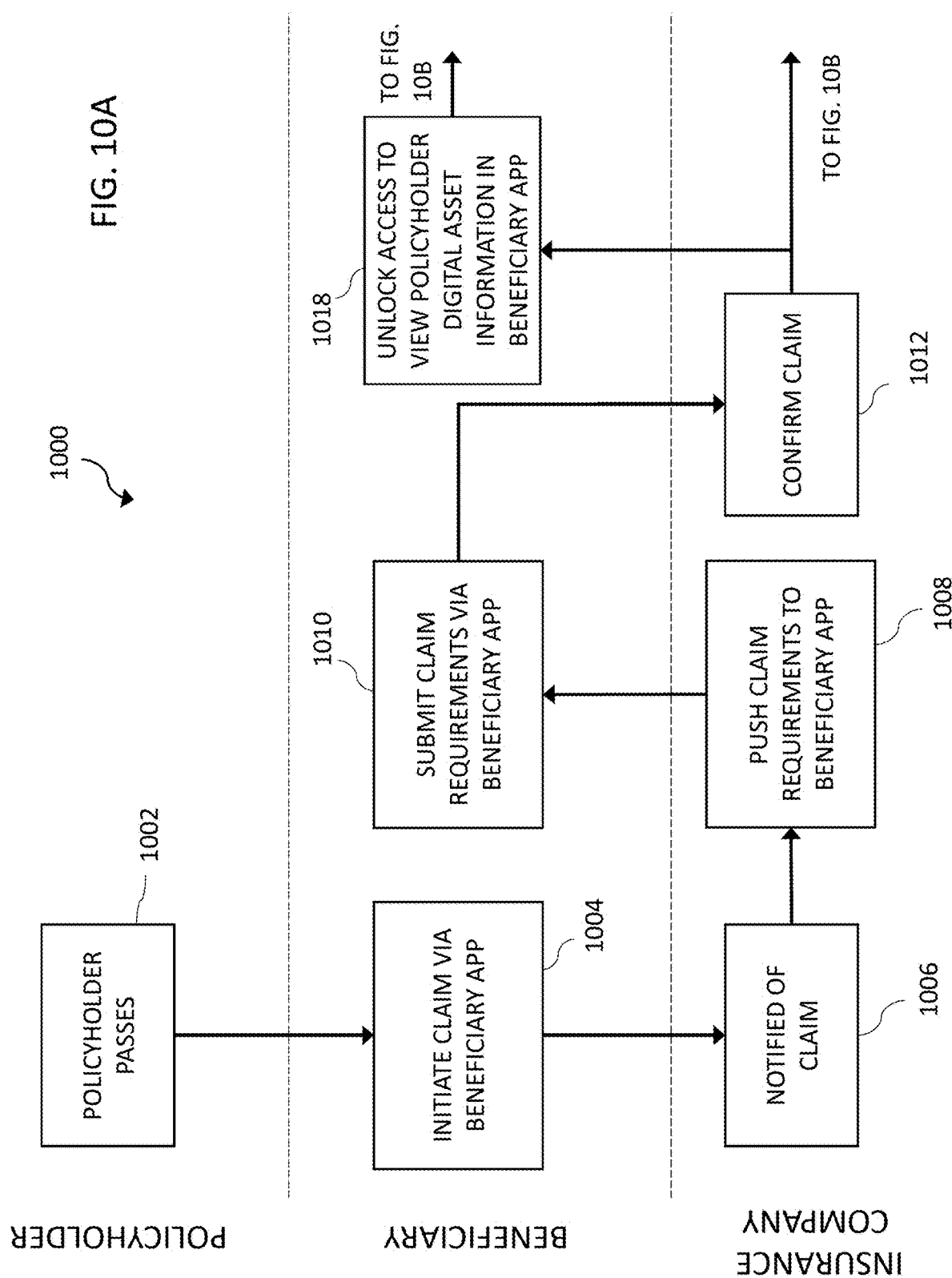

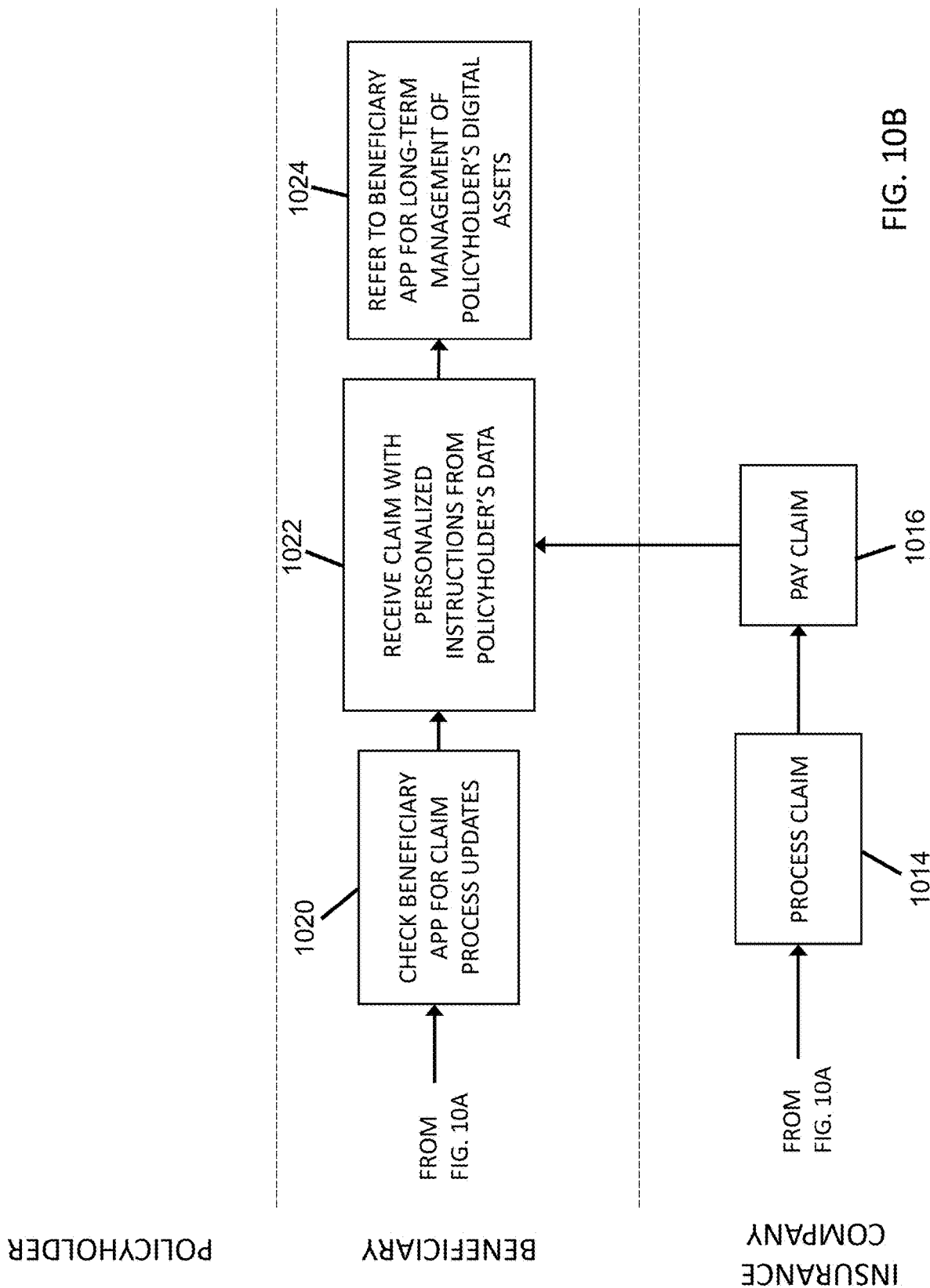

POLICYHOLDER SETUP IN SECURE PERSONAL AND FINANCIAL INFORMATION STORAGE AND CHATBOT ACCESS BY TRUSTED INDIVIDUALS

REFERENCE TO RELATED APPLICATIONS

This application is a continuation of and claims the benefit of U.S. patent application Ser. No. 17/089,388 filed on Nov. 4, 2020 and entitled "Policyholder Setup in Secure Personal and Financial Information Storage and Chatbot Access by Trusted Individuals," which claims the benefit of the following U.S. provisional patent applications: (1) Ser. No. 63/108,528 filed on Nov. 2, 2020 entitled "Secure Personal and Financial Information Storage and Chatbot Access by Trusted Individuals," (2) Ser. No. 62/947,374 filed Dec. 12, 2019 entitled "Secure Personal and Financial Information Storage and Chatbot Access by Trusted Individuals," (3) Ser. No. 62/931,486 filed Nov. 6, 2019 entitled "Secure Personal and Financial Information Storage and Chatbot Access by Trusted Individuals," and (4) Ser. No. 62/930,830 filed Nov. 5, 2019 entitled "Secure Personal and Financial Information Storage and Chatbot Access by Trusted Individuals," all of which are incorporated herein in their entireties and for all purposes.

TECHNICAL FIELD

The present disclosure generally relates to electronic systems and computer-implemented methods for secure data storage and access. More specifically, the present embodiments include systems and methods that enable the secure storage of personal and financial information, and controlled access to the information by trusted individuals.

BACKGROUND

Spouses, executors, beneficiaries and other trusted individuals often face difficult and time-consuming tasks collecting information and documentation used to close decedents' estates. There remains a need for systems and methods to improve this process. Systems and methods of these types should provide a high degree of security.

Conventional estate handling techniques may be inefficient, awkward, time consuming, inaccurate, timely, and/or frustrating for family members. Conventional estate handling techniques may have other drawbacks as well.

SUMMARY

The present embodiments may include a user interface, such as a chatbot (text or voice), which assists a person in gathering and electronically storing documents and other information which would be useful to someone trying to settle their affairs when they pass away or become incompetent. Documents may be stored in a secure electronic storage area, and may be automatically obtained or manually scanned. Information such as what type funeral, where keys are, passwords to electronic accounts, etc. may also be stored. The chatbot may help walk a person through the process and reminds them to deal with steps not taken yet. One or more people, such as family members, children, or beneficiaries, may be given electronic access permission. A chatbot avatar or doppelganger may allow the estate handler to ask questions and gather information from the storage in a simulated chat with the deceased, and facilitate estate handling functionality.

In one aspect, a computer-implemented method of setting up a computer system to provide digital asset storage, management and/or retrieval services in connection with insurance policies is disclosed. The method may comprise: with a policyholder's permission, via one or more processors and/or associated transceivers, enrolling the policyholder in a digital asset storage, management and/or retrieval service, wherein enrolling the policyholder optionally includes establishing an account record associated with the policyholder; receiving from the policyholder, via one or more processors and/or transceivers, information about a beneficiary; accepting and storing, via one or more processors and/or associated transceivers, digital assets associated with the policyholder; sending, via one or more processors and/or associated transceivers, a notification to the beneficiary informing the beneficiary of the opportunity to use the digital asset service; receiving from the beneficiary, via one or more processors and/or transceivers, a request to enroll in the digital asset service; enrolling the beneficiary as the policyholder's beneficiary in the digital asset service, wherein enrolling the beneficiary optionally includes storing information associated with the beneficiary in an account record associated with the policyholder; and sending to the beneficiary, via one or more processors and/or transceivers, information about a beneficiary app that the beneficiary can download onto a communication device and use in connection with the digital asset services.

In another aspect, the computer-implemented method may further comprise receiving from the policyholder, via one or more processors and/or associated transceivers, a request to enroll in the digital asset service. In another aspect, the computer-implemented method of any or all of the above aspects may further comprise sending to the policyholder, via one or more processors and/or associated transceivers, an invitation to enroll in the digital asset service. In another aspect, the computer-implemented method of any or all of the above aspects may comprise an insurance policy including one or more of a life insurance policy, a homeowner or renter insurance policy, a vehicle insurance policy or a medical insurance policy.

In another aspect, the computer-implemented method of any or all of the above aspects may further comprise storing information representative of a virtual personality of the policyholder or a virtual model of the policyholder based upon the digital assets. In another aspect, the computer-implemented method of any or all of the above aspects may comprise digital assets fed into a machine learning module via one or more processors and/or associated transceivers, to create a virtual avatar with a personality similar to the personality of the policyholder. In another aspect, the computer-implemented method of any or all of the above aspects may comprise a beneficiary app that allows the beneficiary to have a conversation with the avatar of the policyholder.

In another aspect, the computer-implemented method of any or all of the above aspects may comprise receiving from the policyholder information about a beneficiary including condition information including one or more of (1) limitations on roles of the beneficiary and/or (2) the types of information that can be provided to the beneficiary. In another aspect, the computer-implemented method of any or all of the above aspects may further comprise prompting the policyholder to provide the information about a beneficiary and the digital assets.

In another aspect, the computer-implemented method of any or all of the above aspects may be offered by a third party to provide services to the policyholder and/or beneficiary.

In another aspect, a computer system for providing digital asset storage, management and/or retrieval services in connection with insurance policies is disclosed. The computer system may comprise one or more local or remote processors, transceivers, servers and/or sensors. The computer system may be configured to: with a policyholder's permission, via one or more processors and/or associated transceivers, enroll the policyholder in a digital asset storage, management and/or retrieval service, wherein enrolling the policyholder optionally includes establishing an account record associated with the policyholder; receive from the policyholder, via one or more processors and/or transceivers, information about a beneficiary; accept and store, via one or more processors and/or associated transceivers, digital assets associated with the policyholder; send, via one or more processors and/or associated transceivers, a notification to the beneficiary informing the beneficiary of the opportunity to use the digital asset service; receive from the beneficiary, via one or more processors and/or transceivers, a request to enroll in the digital asset service; enroll the beneficiary as the policyholder's beneficiary in the digital asset service, wherein enrolling the beneficiary optionally includes storing information associated with the beneficiary in an account record associated with the policyholder; and send to the beneficiary, via one or more processors and/or transceivers, information about a beneficiary app that the beneficiary can download onto a communication device and use in connection with the digital asset services.

In another aspect, the computer system may be further configured to receive from the policyholder, via one or more processors and/or associated transceivers, a request to enroll in the digital asset service. In another aspect, the computer system of any or all of the previous aspects may be further configured to send to the policyholder, via one or more processors and/or associated transceivers, an invitation to enroll in the digital asset service. In another aspect, the computer system of any or all of the previous aspects may comprise an insurance policy including one or more of a life insurance policy, a homeowner or renter insurance policy, a vehicle insurance policy or a medical insurance policy.

In another aspect, the computer system of any or all of the previous aspects may be further configured to store information representative of a virtual personality of the policyholder or a virtual model of the policyholder based upon the digital assets. In another aspect, the computer system of any or all of the previous aspects may be further configured to provide a machine learning module via one or more processors and/or associated transceivers, to create a virtual avatar with a personality similar to the personality of the policyholder based upon the digital assets. In another aspect, the computer system of any or all of the previous aspects may comprise a beneficiary app configured to allow the beneficiary to have a conversation with the avatar of the policyholder.

In another aspect, the computer system of any or all of the previous aspects may be configured to receive from the policyholder information about a beneficiary including condition information including one or more of (1) limitations on roles of the beneficiary and/or (2) the types of information that can be provided to the beneficiary. In another aspect, the computer system of any or all of the previous aspects may be further configured to prompt the policyholder to provide the information about a beneficiary and the digital assets.

The method or system of any or all of the above aspects may be configured to include additional, less, or alternate functionality, including that discussed elsewhere herein.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein:

FIG. 9 depicts an exemplary computer-implemented method of providing digital asset storage, management and retrieval via a chatbot avatar or other digital assistant; and FIGS. 10A and 10B depict an exemplary computer-implemented method of providing digital asset storage, management and retrieval via a chatbot avatar or other digital assistant.

Figure 1:
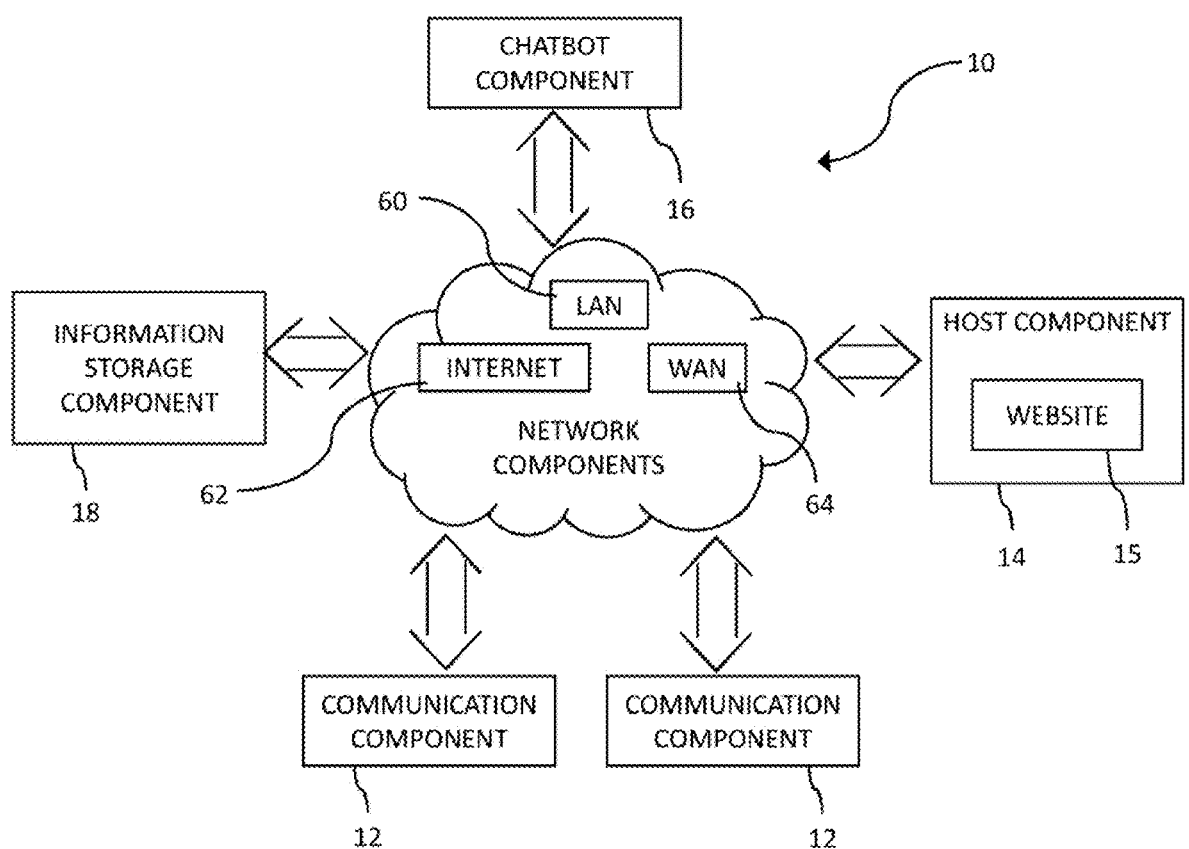
FIG. 1 is a depiction of an exemplary computer network of various components, including the chatbot avatar discussed herein, that may be operated in accordance with computer-implemented methods disclosed herein.

The Figures depict a preferred embodiment of the present invention for purposes of illustration only. One of ordinary skill in the art will readily recognize from the following discussion that alternative embodiments of the structures and methods illustrated herein may be employed without departing from the principles of the invention described herein.

DETAILED DESCRIPTION

The present embodiments may relate to, inter alia, systems and methods that provide computer-implemented interactive estate handling functionality. A chatbot or other digital assistant may walk a person through the process of bequeathing their assets, and reminds them of steps not taken yet. One or more people, such as family members, children, or beneficiaries, may be given electronic access or other permission access the system. In some aspects, a chatbot avatar or doppelganger may allow the estate handler or family member to ask questions and gather information from computer system in a simulated chat with the deceased, and facilitate estate handling functionality.

In one aspect, a computer-implement method and computer system may be configured to facilitate estate handling. An audible or visible chatbot avator or doppelgänger may lead a trustee, beneficiary, or family member through the estate of an impaired or deceased user. A computer system may have been provided with, or gather, sample voice and visual recordings associated with a user that are used to build the chatbot avatar that simulates the user audibly and/or visually. The computer system may have previously prompted the user for necessary items to properly handle their estate, such as information related to financial accounts, loans, insurance policies, etc. and user names and passwords to various electronic accounts.

OVERVIEW

Computer systems and computer-implemented methods disclosed herein relate generally to secure electronic data storage and access. The present embodiments may include systems and methods providing secure electronic storage of information such as, for example, personal and/or financial information of individuals or entities (i.e., storage users). The present embodiments may include systems and methods for providing secure electronic access to the stored information by individuals or entities (i.e., access users) that are trusted by the storage users. These information storage and access services may be provided by a third party as a service product (e.g., through a website). In certain embodiments, the product may be provided by an insurance company or a financial services company to storage users (e.g., for a fee, or in connection other offered products such as life insurance or investment services).

Access to the stored information by the access users, for example timing of the access and authorization credentials, may be controlled by the storage users. The access users may obtain access to the stored information through the use of networked communication devices such as mobile devices and automated personal assistants. Communications using the communication devices, for example SMS-based text and natural language conversations, may be through a chatbot that simulates the storage user associated with the stored information, such as a chatbot avatar.

In some embodiments, the systems and methods are used by trusted access users such as spouses, executors and beneficiaries to obtain access to storage users' stored personal and/or financial information following significant or other triggering events, such as for example upon doctors' orders, incapacitation or passing away of the storage users. For instance, the access users may obtain chatbot access to a decedent storage user's stored personal and financial information by an app that is made accessible to the access user and loaded onto their communication device before or following the storage user passing away.

The systems and methods described herein offer important advantages. Trusted individual access users such as beneficiaries can easily, efficiently and quickly request and obtain important information. Those access users can process that information in an appropriate manner (e.g., relay it to others such as lawyers, agents and accountants). Difficulties associated with conventional approaches, such as digging through various different files and making many phone calls, may be alleviated. The information may be securely stored and released in controlled manners to authorized individuals, such as family members. The product may be easy to use by both the storage users and access users, as well as efficient to operate and provide.

Exemplary Networked System

FIG. 1 is a diagrammatic illustration of embodiments of a networked system 10 that may be operated in accordance with computer-implemented methods disclosed herein to provide secure information storage and access services. The illustrated embodiments include one or more user communication components 12 (two are shown), host component 14, chatbot component 16 and information storage component 18 coupled by network components 20. As described in greater detail below, host component 14, which may include a website 15 in certain embodiments, may be operated by an entity providing the product, such as for example an insurance company.

Host component 14 may provide certain control and communications operations of the system 10. Information storage component 18 may store information used by the system 10, including personal and financial information of users. Communication components 12 may provide the various users, including the individuals storing information and the trusted accessing individuals, with interfaces to access the system 10. Chatbot component 16 may provide the chatbot communications functionality discussed herein, including the avatar chatbot functionality.

Host component 14, chatbot component 16 and information storage component 18 are functional elements, and may be elements of a common (i.e., one) computing system or elements of two or more computing systems (i.e., each component may be implemented in a separate computing system). For example, in certain embodiments the host component 14, chatbot component 16 and information storage component 18 may be components of a networked computer system operated by an entity, such as an insurance or financial services company, that offers and provides the secure information storage and access product. In other embodiments these components 14, 16, 18 are provided by a third party or by an on-demand cloud computing platform. In some embodiments, components 14, 16 and 18 may be implanted in whole or in part as hardware modules.

Exemplary Computer System

Figure 2:
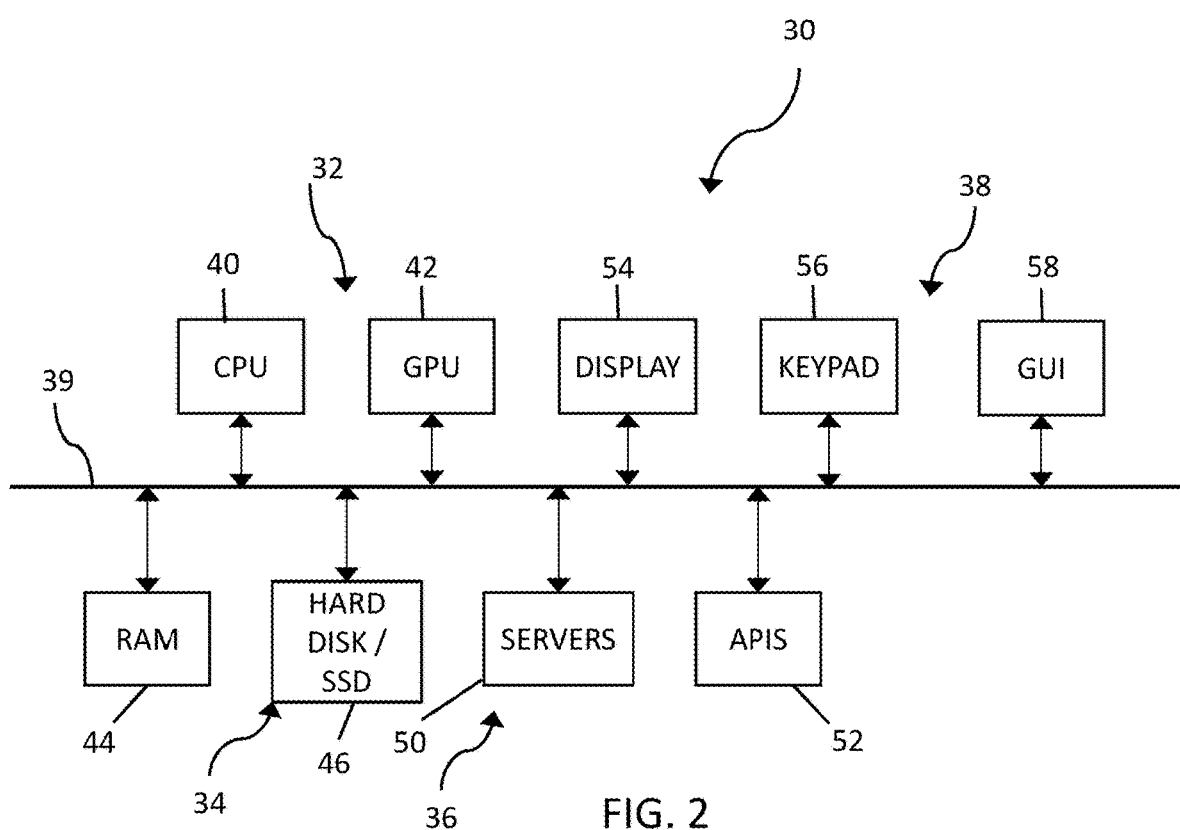
FIG. 2 is a depiction of an exemplary computer system that may be used in connection with the exemplary computer network to provide the chatbot avatar and estate handling functionality detailed herein, and to facilitate the related computer-implemented methods.

FIG. 2 is a diagrammatic illustration of an exemplary computer system 30 that may be used to implement host component 14, chatbot component 16 and/or information storage component 18 in accordance with certain embodiments to provide the secure information storage and access methods described herein. The illustrated embodiments of computer system 30 may include processing components 32, storage components 34, network interface components 36 and user interface components 38 coupled by a system network or bus 39.

Processing components 32 may, for example, include central processing unit (CPU) 40 and graphics processing unit (GPU) 42, and provide the processing functionality of the host component 14, chatbot component 16 and/or information storage component 18. The storage components 34 may include RAM memory 44 and hard disk/SSD memory 46, and provide the storage functionality of the host component 14, chatbot component 16 and/or information storage component 18.

For example, operating system software used by the processing components 32 and one or more application software packages used by the host component 14 to implement methods described herein may be stored by the storage component 18. By way of example, software executed to provide the text and speech/natural language functionality, and the user account setup, user information collection and storage, trusted individual setup, trusted access user setup and chatbot communication processes described herein may be stored by the storage components 34. User profile information used by the chatbot component 16 and user information stored by the information storage component 18 may also be stored by the storage components 34.

In some embodiments, the network interface components may include one or more web servers 50 and one or more application programming interfaces (APIs) 52 to implement interfaces between the host component 14, chatbot component 16 and information storage component 18 and the network components 20. Examples of user interface components 38 may include display 54, keypad 56 and graphical user interface (GUI) 58. Embodiments of computer system 30 may include other conventional or otherwise known components to provide secure information storage and access services in accordance with embodiments described herein.

Network components 20 may be functional elements, and may include one or more networks for connecting the communication components 12, host component 14, chatbot component 16 and information storage component 18. In some embodiments, for example, the network components 20 may include one or more local area networks (LAN) 60, internet 62 and one or more wide area networks (WAN) 64 coupling the host component 14, chatbot component 16 and information storage component 18. LAN 60 may, for example, couple the host component 14, chatbot component 16 and information storage component 18 to one another and to the internet 62. WANs 64, which for example include cellular networks, may couple communication components 12 to the internet 62. Other configurations of network components 20 are contemplated.

Communication components 12 may include devices operated by users to interface with other components such as host component 14, chatbot component 16 and information storage component 18 and perform information storage and access services in accordance with methods described herein. For example, communication components 12 may include commercially available mobile devices such tablets, phones, and laptop computers. Communication components 12 may also include desktop computers and virtual assistants such as intelligent virtual assistants (IVAs) or intelligent personal assistants (IPAs) (e.g., Amazon Echo) incorporated into or coupled to such mobile and other devices.

Information storage component 18, as noted above, is used to store information of users. For purposes of description, and to distinguish users such as individuals and/or entities storing information from users such as trusted individuals and/or entities that may obtain access to the stored information, the term "storage users" as used herein refers to the users storing information. For purposes of description, the term "access users" refers to the users that access the information stored on behalf of the storage users. As used herein, the terms "information" and "stored information" can include any and all information and documents stored in the information storage component 18 by or on behalf of the storage users.

Personal and/or financial information is an example of a category of such information that may be stored. Specific but non-limiting examples of such information include one or more of records and/or documents associated with: property and casualty (P&C) insurance policies, life insurance policies, brokerage and other investment accounts, individual securities (e.g., stocks, mutual funds), mortgages and other loans, pensions, social security accounts, wills, birth certificates, marriage licenses, children and grandchildren, burial plans, utility providers and professional service providers such as accountants, financial advisors, securities brokers and lawyers.

Conventional or otherwise known data structures may be used by the storage component 18 to create logical files or other organizations for the stored information. Conventional or otherwise known physical and cyber security tools may be used to protect the information storage component 18 and information stored therein, as well as the other components of networked system 10.

Chatbot component 16 may be configured with personal user profile information of the storage users to enable electronic communications (e.g., conversations by text messages or audibly by speech through natural language processing) with access users in a manner that may simulate the behavior and/or communication characteristics of the storage users. As described in greater detail below, when using the product following a storage user's passing, the access users may thereby obtain access to personal and financial information of the storage user through a simulated personalized conversation with the storage user (such as via a chatbot avatar).

The personal information used by the chatbot component 16 may be reflected by the storage user's digital "footprint" and can be obtained, for example, from emails, texts, tweets, snapchats and other electronic communications of the storage user (e.g., from the storage user's social media accounts). This user personal profile information may be configured into the chatbot component 16 during the storage user's lifetime and/or following the storage user's passing. Conventional or otherwise know chatbot components 16, including those using artificial intelligence (AI) methodologies, may be used in connection with embodiments described herein.

Host component 14 may provide an interface platform such as website 15, and control and processing functions in connection with the information storage and access product. In certain embodiments, host component 14 coordinates communications between the communication components 12 and chatbot 16 and information storage component 18. Communications coordinated by the host component 14 may include, for example, commands and information received from storage users and access users, and the transmission of instructions, information and apps to the storage users and access users (e.g., in response to such commands and information).

In some aspect, certain communications to and/or from communication components 12 of storage users and access users are made though the website 15. Certain embodiments may also include communications not made through the website 15. For example, in some embodiments, information of storage users requested by access users following the storage user's passing may be transmitted from information storage component 18 through communications channels that do not include website 15.

In some embodiments, host component 14 coordinates the operation of chatbot component 16 and information storage component 18 in response to commands and information received from communication components 12, and provide processing functionality to cause appropriate responsive actions to such commands and information. As described in greater detail below, for example, host component 14 may perform and/or control storage user account setup processes, personal and financial information collection processes, access user setup and notification processes, and chatbot information access processes provided in connection with the product. The computer system, network, and components may be configured to include additional, less, or alternate functionality, including that discussed elsewhere herein.

Exemplary Storage User Account Setup Process

Figure 3:
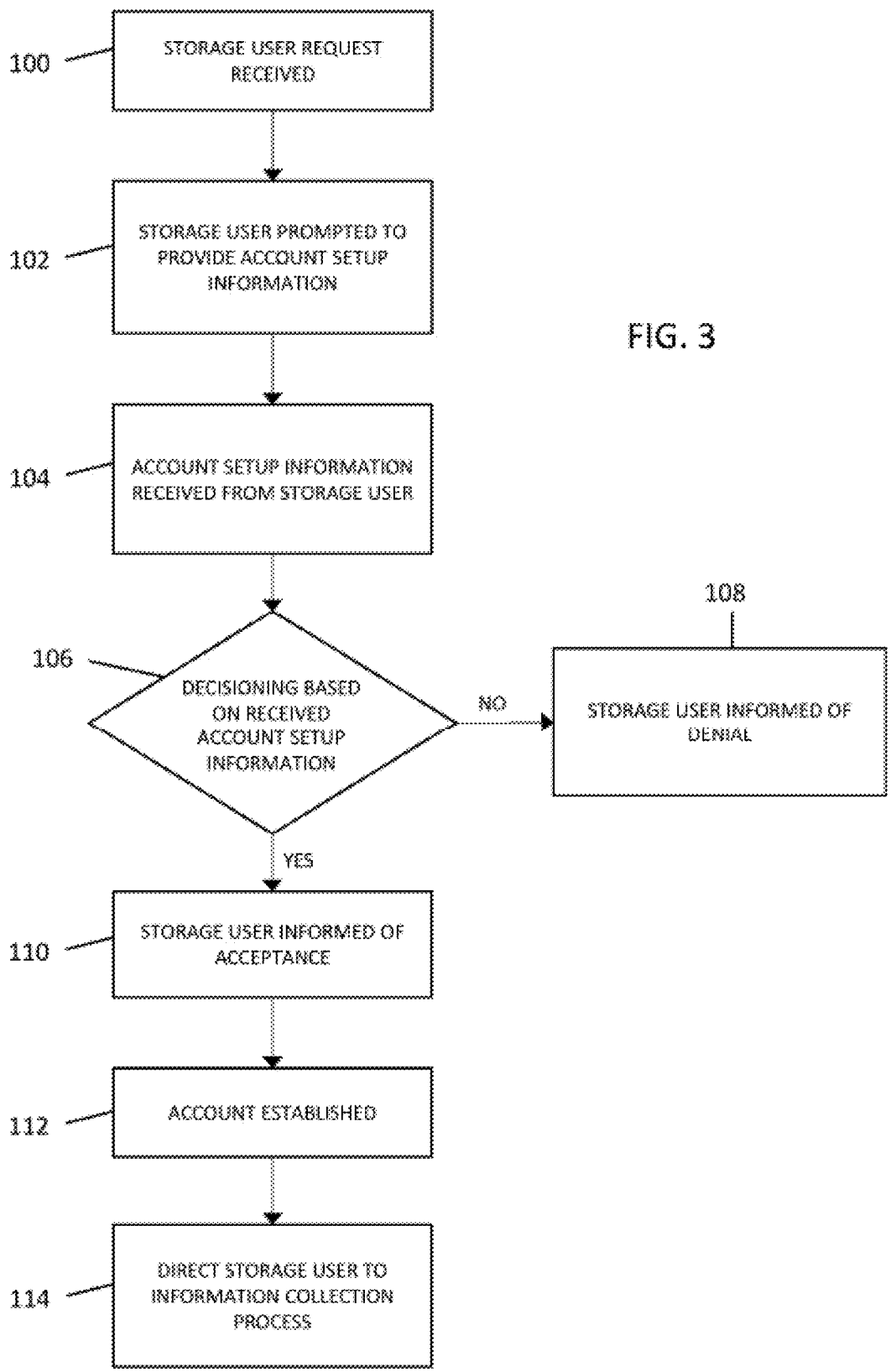
FIG. 3 illustrates an exemplary computer-implemented method that may be performed through the use of networked system to onboard storage users that want to utilize the information storage and access product.

FIG. 3 illustrates an exemplary computer-implemented method that may be performed through the use of networked system 10 to onboard storage users that want to utilize the information storage and access product. As shown at step 100, a user that wants to subscribe to or otherwise make use of the product accesses the host component 14, for example the website 15, through a communication component 12 to request an account.

In response, the host component 14 may provide the user with prompts requesting information needed to set up a storage user account as shown by step 102. Requested information may include, for example, contact information, and information about whether the requester has an established and current relationship with the product provider. The prompts may be provided by conventional or otherwise known approaches such as a document with fillable text form or audible voice requests.

As shown by step 104, information is received by the host component 14 in response to the requests (e.g., in text or voice response form). The host component 14 may perform decisioning based upon the received information to determine whether to accept the requester at step 106. In some embodiments, the product provider may accept as subscribers or other customers only storage users with which it has a current established relationship. Product providers that are insurance companies may, for example, provide the product only to existing customers.

In certain embodiments of these types the host computer 14 evaluates the received information along with information representative of existing customers to determine whether the requester is an existing customer. If the decisioning step determines that requester does not meet requirements for the product, for example if the requester has not provided sufficient contact information and/or has been determined to not be a current customer, the requester may be sent a communication stating that the request is denied as shown by step 108.

If the decisioning step determines that the requester meets the requirements for the product, a communication informing the requester of the acceptance may be sent as shown by step 110. Host component 14 may establish and store an account record for the storage user as shown by step 112. The account record may include an account identifier, such as an account number. As shown by step 114, the storage user may be sent a message informing the storage user that they should complete an information collection process to make the account operational. The account record may be communicated to the storage user in the message of step 114. The computer-implemented method may be implemented via one or more local or remote processors, servers, sensors, and/or transceivers, and include additional, less, or alternate functionality, including that discussed elsewhere herein.

Exemplary Personal & Financial Info Collection Setup Process

Figure 4:
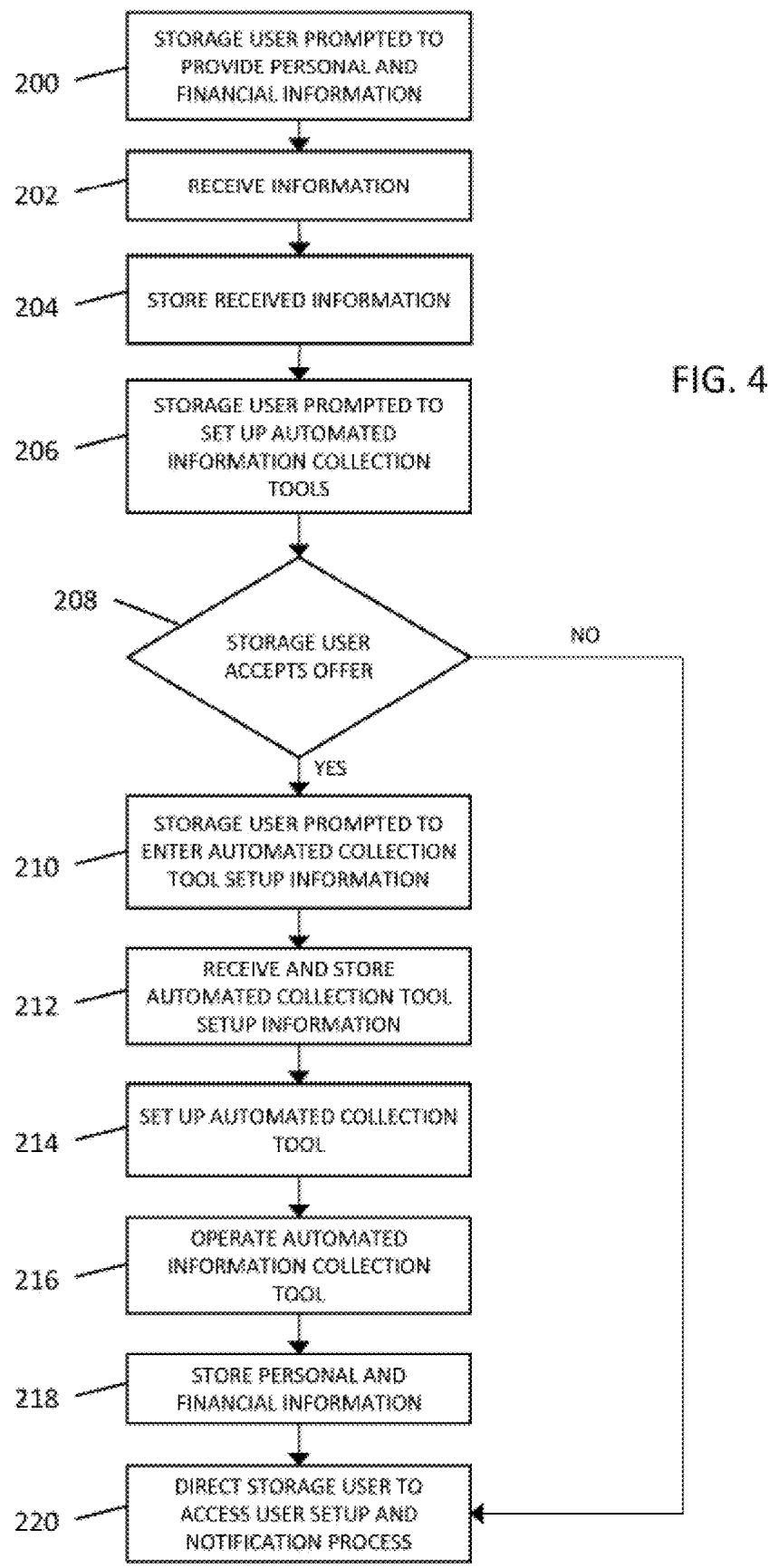
FIG. 4 illustrates an exemplary computer-implemented method that may be performed though the use of networked system to collect the personal and financial information the storage user wants to store in the system.

FIG. 4 illustrates an exemplary computer-implemented method that may be performed though the use of networked system 10 to collect the personal and financial information the storage user wants to store in the system. As shown by step 200, the host component 14 may provide the user with prompts requesting the information. In some embodiments, host component 14 may provide the prompts by a user-friendly template that allows the storage user to conveniently and accurately submit the information. The template may be provided by conventional or otherwise known approaches, such as a fillable text form or audible voice requests, and fields for the attachment of any documents included in the information.

In some embodiments, the host component 14 may request additional information to be associated with individual items of the personal and/or financial information. Examples of such additional information include condition information such as specific access users that the associated information can or cannot be released to, and other conditions (e.g., timing) regarding the release of the information. In some embodiments, host component 14 may provide instructions, e.g., by text or speech, to assist the storage user with the collection of the information. As shown by steps 202 and 204, the host component 14 may store the personal and financial information it receives from the storage users (e.g., in the information storage component 18). Any received additional information associated with the received personal or financial information may also be stored.

As shown by step 206, in some embodiments the host component 14 may provide the storage user with a communication offering them the option to set up one or more automated information gathering tools to collect one or more items of information. The information gathering tools may, for example, be used to perform the initial collection of the information (e.g., as an alternative to receiving the information, including any associated documents, as part of steps 200 and 202), and/or to periodically collect and thereby update the information following its initial collection.

If the storage user responds by accepting the offer as shown at step 208, host component 14 may send a communication to the storage user requesting setup information from the storage user needed to set up the tool as shown at step 210. The requested setup information may include, for example, identification of the location of the information (e.g., a third party website address and the storage user's account information at which the information to be requested can be found), any authorization credentials (e.g., user name, password) required to gain electronic access to the information, and/or the periodicity by which the information should be collected (e.g., once, monthly, annually). If the host component 14 receives a communication from the storage user declining the opportunity to set up automated information collection tools, the host component may take no further action with respect to that functionality in the information collection process.

If the requested setup information is received, it may be stored in association with the storage user's account as shown by step 212. Host component 14 may use the setup information to configure a data collection tool such as an application programming interface (API) as shown at step

214. The host component 14 may operate the automated information collection tools in accordance with the stored setup information to collect the information and associated documents as shown by step 216, and store the received information as shown by step 218. In some embodiments, text and/or voice response communication approaches may be used in connection with steps 206-218. As shown by step 220, the storage user may be sent a message informing the storage user that they should complete an access user setup and notification process to make the account operational.

In some embodiments, host component 14 may provide prompts requesting information (e.g., social media accounts, email addresses) used to configure the personal profile of the chatbot component 16 for the storage user, and store any such received information. Methods substantially the same as or similar to those described above in connection with FIG. 4 may also be used for this purpose. The computer-implemented method may be implemented via one or more local or remote processors, servers, sensors, and/or transceivers, and include additional, less, or alternate functionality, including that discussed elsewhere herein.

Exemplary Access User Setup and Notification Process

Figure 5:
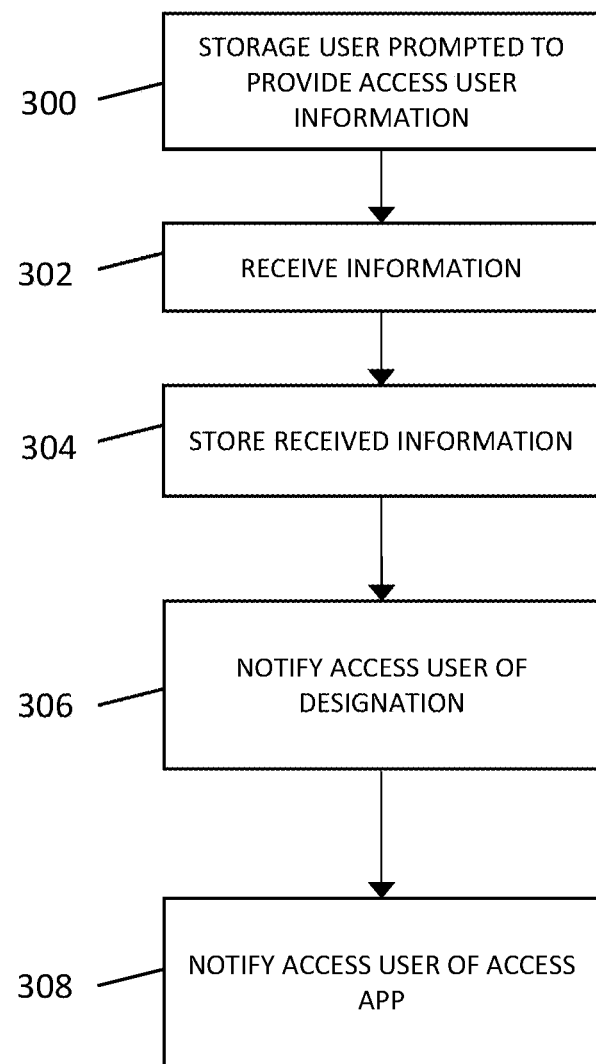
FIG. 5 illustrates an exemplary computer-implemented method that may be performed through the use of networked system to set up the access users for the storage user's account, and to notify the access users of their designation as an access user and associated roles.

FIG. 5 illustrates an exemplary computer-implemented method that may be performed through the use of networked system 10 to set up the access users for the storage user's account, and to notify the access users of their designation as an access user and associated roles. As shown by step 300, the host component 14 may provide the storage user with prompts requesting information on access users the storage user desires to designate. The requested access user information may include, for example, identification of the access users, their contact information (e.g., email addresses and text message addresses) and their relationship to the storage user.

The requested access user information may also include additional information about the access users. Examples of such additional information include condition information, such as limitations on the roles of the trusted individuals and/or the types of stored information of the storage user that may be provided to the access users. For example, access users having certain roles such as executors or those having power of attorney may be set up to have access to all stored information of the storage user.

Access users with other and perhaps more limited roles or relationships to the storage user, such as for example an accountant, may be provided access to limited amounts of the stored information such as information about utilities that need to be paid while an estate is being closed. In these and other embodiments, different access users of a given storage user may also be set up to obtain access to the stored information upon different triggering events. For example, for a given storage user, one or more first access users may be set up for access to stored information upon the issuance of a doctor's order, and one or more second access users, including access users different than the first access users, may be set up for access to stored information upon the storage user's passing.

In some embodiments, host component 14 may provide the prompts by a user-friendly template that allows the storage user to conveniently and accurately submit the access user setup information. The template may be provided by conventional or otherwise known approaches, such as fillable text form or audible voice requests. In some embodiments, host component 14 may provide instructions, e.g., by text or speech, to assist the storage user with the collection of the access user setup information. As shown by steps 302 and 304, the host component 14 may store the trusted individual information it receives from the storage users. Any received additional information associated with the received access user setup information may also be stored.

Host component 14 may notify access users that they have been designated an access user as shown by step 306. The notifications may, for example, be transmitted to the one or more of the access user's communication components 12 using the stored contact information associated with the storage user's account. Information that may be included in the notification includes, for example, the name of the associated storage user, contact information for the storage user, the roles, including any conditions, that have been assigned to the access user, a description of the triggering event that will enable to access user to access the product, description of the product and instructions for use of the product, authorization credentials such as user names and passwords.

In some embodiments, the notification may include a link to a website (e.g., website 15) as a source of the information. Additionally or alternatively, in some embodiments, the notification may occur at the time that the access user setup is completed, at the time of the triggering event, or both. Additionally or alternatively, in certain embodiments, the host component 14 periodically (e.g., annually) sends notifications to the access users.

In some embodiments, the access users may interface with the host component 14 using access apps on their communication components 12. Information about the access app, including instructions on how to download (optionally including a link to the source) and use the app, may be transmitted by the host component 14 as shown by step 308. In certain embodiments, host system 14 may transmit the information about the app, or the app itself, to the access user with one or more of the notifications described above in connection with step 306.

In some embodiments, such as embodiments where the access users obtain access to the access app before the occurrence of the triggering event associated with the storage user, the access app may not allow the access user to access the stored information of the storage user. In these and other embodiments, the access app may allow the access user to access other information about the product and their role (e.g., through website 15) without allowing access to the stored information of the storage user. The computer-implemented method may be implemented via one or more local or remote processors, servers, sensors, and/or transceivers, and include additional, less, or alternate functionality, including that discussed elsewhere herein.

Exemplary Chatbot Information Access Process

Figure 6:
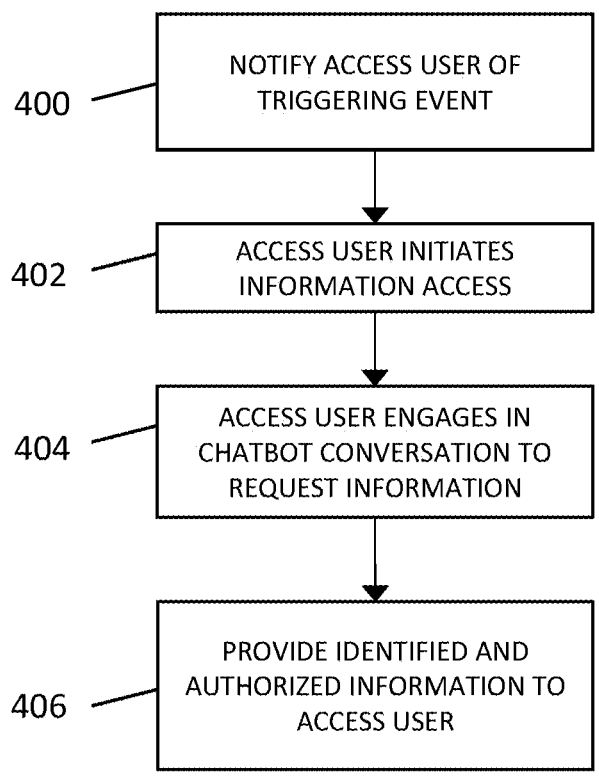
FIG. 6 illustrates an exemplary computer-implemented that may be performed through the use of networked system 10 to enable access users to access the stored information of storage users.

FIG. 6 illustrates an exemplary computer-implemented that may be performed through the use of networked system 10 to enable access users to access the stored information of storage users. Upon the occurrence of the triggering events associated with storage users, host component 14 may allow the access users to access the stored information of the storage users in a manner consistent with the associated conditions of the storage users' accounts.

In some embodiments, host component 14 may notify access users of the occurrence of the trigger event as shown at step 400. The notice may include information about the nature of the triggering event, including the time of the event, and optionally other information such as that described above in connection with FIG. 5.

For example, in some embodiments where the access app is not provided to the access user before the triggering event, a link and instruction on how to download the access app may be included. In some embodiments where the access app was previously downloaded by the access users, the notice may include instructions on how to use the access app. Additionally or alternatively, in some embodiments, for example, the notice may include instructions on how to use the communication component 12 to carry on a conversation with chatbot component 16 to access the stored information.

The access user may initiate an information access session as shown by step 402. Access user credentials, such as user name and password, may be required by the host component 14 before the host component initiates such a session. In addition to or alternatively, access credentials may be incorporated into the access app. During the information access session, the access user may request information associated with the storage user.

In some embodiments, the access user engages in a conversation facilitated by the chatbot component 16 to request information of the storage user, as shown by step 404. Such a conversation may be performed by text communications (e.g., SMS text) or by speech (e.g., natural language processing). During such conversations, the responses from host component 14 to the access user will be personalized to simulate characteristics of the storage user (e.g., will have the look and feel of a text or voice conversation). The access user may feel that they are conversing directly with the storage user. In other words, the chatbot may be programmed to be the avatar or doppelgänger of a deceased storage user.

Host component 14 may search for the requested information. Identified requested information that the access user is authorized to receive may be transmitted or otherwise provided to the access user as shown by step 406. In some embodiments, the requested information may be transmitted in text or speech, as numerical information (e.g., account numbers, phone numbers, dates) or words or short phrases such as names, locations. In these and other embodiments the host component may transmit the requested information in the form of documents (e.g., in pdf form) or links to such documents. The access user may not know what types of information the storage user has stored, or what types of information is available to the access user.

In some embodiments, host component 14 may transmit requested and identified information to the access user only if the access user is authorized to receive such information (e.g., based upon any condition information stored in connection with the storage user's account). The computer-implemented method may be implemented via one or more local or remote processors, servers, sensors, and/or transceivers, and include additional, less, or alternate functionality, including that discussed elsewhere herein.

Exemplary Chatbot Conversation with Chatbot Avatar

Figure 7:
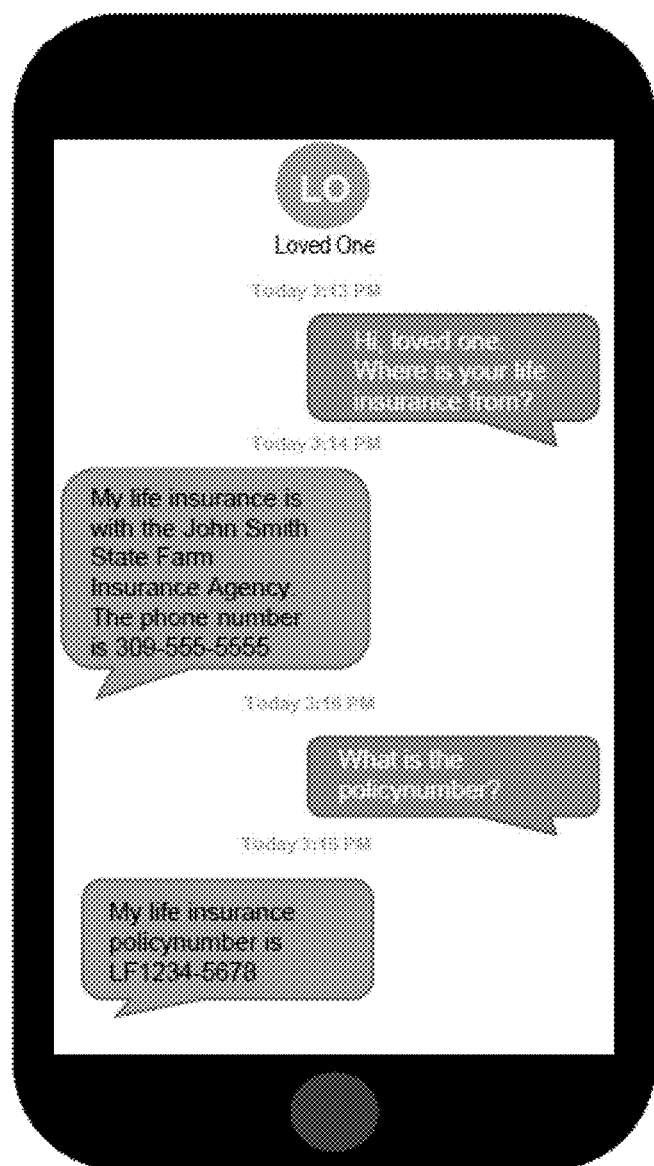
FIG. 7 is an exemplary graphical illustration of a chatbot conversation between an access user and a simulated version of a storage user through the use of networked system.

FIG. 7 is an exemplary graphical illustration of a chatbot conversation between an access user and a simulated version of a storage user through the use of networked system 10. The conversation is shown on the access user's mobile phone for purposes of illustration. Although the conversation is shown in text form in FIG. 7, the same conversation may be additionally or alternatively be carried out audibly by speech in other embodiments. By this conversation the access user identified and received the issuing company name, contact information and policy number for a life insurance policy of the storage user.

The following text is another example of a chatbot conversation that an access user (Sam in this example), may have through the use of networked system 10 with a storage user (Pam in this example):

Sam: "Pam, this is Sam, your brother. I'm so sorry to have to talk with you now, so soon after your unexpected passing."

Pam: "Thanks for the condolences Sammy."

Sam: "You told me some time ago that I was appointed as the executor of your estate. We did not discuss the details of that appointment. Can you tell me where I can find your will?"

Pam: "You bet. A copy of my will can be accessed through the following link. www.foreverchat.org. My attorney is Jan Anderson at the Newtown office of Johnson and Anderson. Her phone number is 312 776 7219."

Exemplary Computer-Implemented Methods

Figure 8:
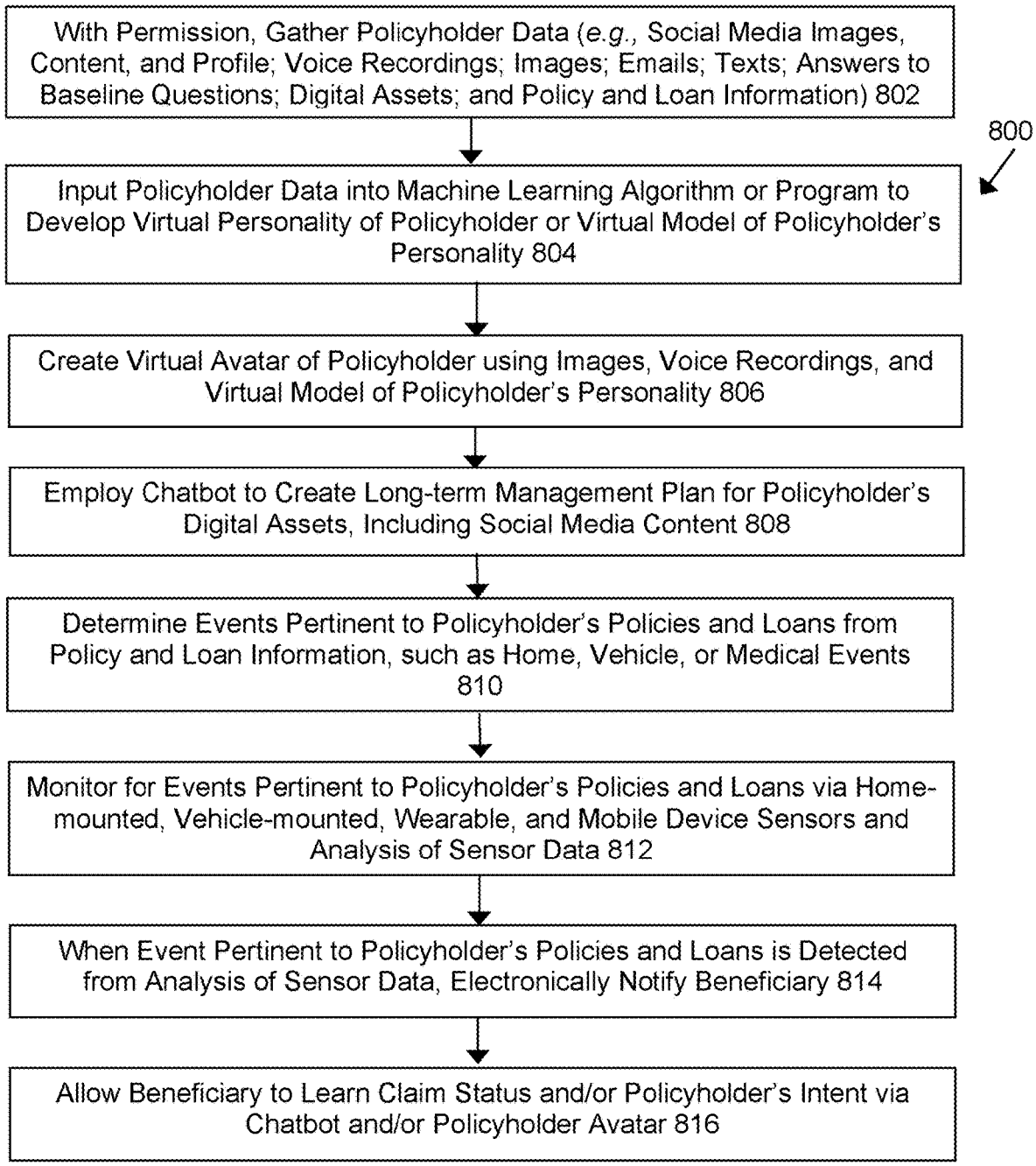
FIG. 8 depicts an exemplary computer-implemented method of detecting insurance-related events, and then handling insurance claims via a chatbot avatar.

FIG. 8 depicts an exemplary computer-implemented method of detecting insurance-related events, and then handling insurance claims via a chatbot avatar 800. The method may be implemented via one or more local or remote processors, transceivers, sensors (such as wearables, mobile device sensors, vehicle sensors, home sensors, drone sensors, etc.), and/or servers. The method 800 may include, via one or more processors, transceivers, sensors, and/or servers, (1) with customer permission or affirmative consent, gathering policyholder data 802. For instance, social media images, content, profile information, and other digital data associated with the customer may be gathered. The policyholder data may also include voice recordings, images, videos, emails, texts, answers to baseline questions, digital assets, and policy and loan information.

The method 800 may include, via one or more processors, transceivers, sensors, and/or servers, inputting the policyholder data and/or digital assets into a machine learning algorithm or program to develop a virtual personality of the policyholder or virtual model of a policyholder's personality 804.

The method 800 may include, via one or more processors, transceivers, sensors, and/or servers, creating a virtual avatar of the policyholder using images, voice recordings, and the virtual model of the policyholders' personality 806. For instance, a chatbot avatar of the policyholder may be created that sounds and/or looks similar to the policyholder.

The method 800 may include, via one or more processors, transceivers, sensors, and/or servers, employing a chatbot to create a long-term management plan for a policyholder's digital assets, including social media context 808.

The method 800 may include, via one or more processors, transceivers, sensors, and/or servers, determining or detecting events pertinent to the policyholder's policies and loans from policy and loan information, such as home, vehicle, or medical events 810. For instance, vehicle telematics data (such as speed, location, acceleration, cornering, or braking data), vehicle sensor (including audio and image) data, home sensor (including audio and image) data, home telematics data (electrical and water usage data, occupancy data, motion data, etc.), wearable sensor data, mobile device sensor or other data, smart watch data, smart glasses data, and/or other sensor data may be collected and analyzed to determine insurance-related events (such as damage to vehicles or homes, or medical events).

Additionally or alternatively, the method 800 may include, via one or more processors, transceivers, sensors, and/or servers, monitoring for events pertinent to the policyholder's policies and loans from policy and loan information 812. For instance, vehicle telematics data (such as speed, location, acceleration, cornering, or braking data), vehicle sensor (including audio and image) data, home sensor (including audio and image) data, home telematics data (electrical and water usage data, occupancy data, motion data, etc.), wearable sensor data, mobile device sensor or other data, smart watch data, smart glasses data, and/or other sensor data may be continuously collected and analyzed to determine insurance-related events (such as damage to vehicles or homes, or medical events).

The method 800 may include, via one or more processors, transceivers, sensors, and/or servers, when an event pertinent to the policyholder's policies and loans is detected from analysis of sensor or other data, a beneficiary or family member be electronically notified 814. For instance, an electronic message may be transmitted to their mobile device.

The method 800 may include, via one or more processors, transceivers, sensors, and/or servers, allowing the beneficiary to learn a claim status and/or policyholder's intent via the chatbot avatar and/or policyholder avatar 816. For instance, the chatbot avatar may have a voice and personality similar to that of the policyholder. The method may include additional, less, or alternate actions, including those discussed elsewhere herein.

In one aspect, an exemplary computer-implemented method of detecting insurance-related events, and then handling insurance claims via a chatbot avatar may be provided. The method may be implemented via one or more local or remote processors, transceivers, servers, and/or sensors. The method may include: (1) with a policyholder's permission and affirmative consent, building, via one or more processors and/or associated transceivers, a policyholder profile and/or online policyholder account for the policyholder based upon policyholder input, the policyholder profile including characteristics of the policyholder and policy information; (2) accepting, via one or more processors and/or associated transceivers digital, assets uploaded by the policyholder, and associating the digital assets with the policyholder profile; (3) upon the policyholder selecting a beneficiary, contacting, via one or more processors and/or associated transceivers, the beneficiary via electronic communication, and then granting the beneficiary electronic access to the policyholder account via a beneficiary app; (4) detecting, via one or more processors and/or associated transceivers, an event associated with the policyholder, such as via one or more home, vehicle, wearable, and/or mobile device sensors, or otherwise receiving notification of the event associated with the policyholder, such as via electronic communication with the policyholder's or a beneficiary's mobile device; (5) sending, via one or more processors and/or associated transceivers, an electronic notification of the event to the beneficiary; (6) initiating, via one or more processors and/or associated transceivers, a claim based upon the policy and/or the event; and/or (7) displaying, via one or more processors and/or associated transceivers, the status of the claim via the beneficiary app, or verbally relaying the status of the claim to the beneficiary via the beneficiary app or chatbot, or otherwise allowing, via one or more processors and/or associated transceivers, the beneficiary to track the status of the claim via the beneficiary app to facilitate handling claims in efficient and convenient manner and/or enhance the customer experience. The method may include additional, less, or alternate actions, including those discussed elsewhere herein.

For instance, the digital assets may include: (a) financial statements, financial account statements, tax information and returns, and/or one or more deeds; and/or (b) social media content, telephone voice recordings, and/or emails associated with the policyholder.

The digital assets may be fed into a machine learning algorithm, model, module, or program, via one or more processors and/or associated transceivers, to create a virtual audible and/or computer-generated visual avatar with a personality similar to the personality of the policyholder. The machine learning algorithm, model, module, or program employs supervised or unsupervised machine learning techniques.

The beneficiary app may allow the beneficiary to have a conversation with the chatbot avatar of the policyholder. The digital assets may include one or more passwords to one or more online accounts of the policyholder.

The claim may relate to a life insurance or health insurance policy. Additionally or alternatively, the claim may relate to a homeowners or auto insurance policy. The claim may relate to an auto insurance policy, and vehicle telematics (such as location, speed, acceleration, braking, and cornering data) or home sensor data (images, audio, occupancy information, etc.) may be analyzed to estimate vehicle damage and repair or replacement costs. Alternatively, the claim may relate to a homeowners insurance policy, and vehicle telematics or home sensor data may be analyzed to estimate home damage and repair or replacement costs.

The digital assets may include monthly, periodic, or otherwise recurring bills, such as telephone, cable, electricity, and water bills, and/or auto or home loan information and statements. The event may be a sickness, illness, or passing away of the policyholder.

The method may further include allowing, via one or more processors and/or associated transceivers, the beneficiary to upload necessary documents, such as a death certificate or doctor's statement, to the online policyholder account. Additionally or alternatively, the method may include, via the one or more processors and/or associated transceivers, allowing the beneficiary to learn the status of the claim via a conversation with a chatbot, and receive answers to questions regarding the claim verbally from the chatbot.

The method may include, via the one or more processors and/or associated transceivers, verbally informing the beneficiary of the actual or likely wishes of the policyholder for various assets via a conversation with the avatar of the policyholder. Additionally or alternatively, the method may include, via the one or more processors and/or associated transceivers, guiding the policyholder thru the process of creating a will and/or identifying assets to be transferred to various beneficiaries via a chatbot. The will may provide for long-term management of the policyholder's social media accounts and digital assets, including digital images. The method may include, via a chatbot, posing several questions to the policyholder to build a baseline personality for the avatar of the policyholder.

The event may be a vehicle event (e.g., vehicle collision associated with a vehicle covered by an auto insurance policy), and the event and/or vehicle damage may be detected by one or more vehicle-mounted sensors or mobile device sensors. Additionally or alternatively, the event may be a home event (e.g., damage to a home covered by a homeowners insurance policy, or an apartment or condo covered by a policy, or personal belongings damaged that are covered by a personal articles policy), and damage to a home, apartment, condo, and/or personal belongings may be detected via one or more home-mounted sensors, vehicle-mounted sensors, and/or mobile device sensors.

Additionally or alternatively, the event may be a medical event associated with the policyholder and covered by the policy, and the medical event is detected by one or more home-mounted sensors, vehicle-mounted sensors, mobile device sensors, smart glasses, smart watches, and/or wearable sensors.

In another aspect, a computer-implemented method for facilitating estate handling or claim handing via a chatbot avatar having the personality and voice mimicking that of an insured may be provided. The method may be implemented via one or more local or remote processors, transceivers, servers, and/or sensors. The method include, via the one or more local or remote processors, transceivers, servers, and/ or sensors, (1) receiving and/or storing personal and/or financial information received from an insured (or first or storage user); (2) generating a chatbot avatar for the insured based upon the personal information received from the insured; (3) receiving a request from an access user (or second user) to access the stored information; (4) communicating with the access user by a simulated conversation with the insured via the chatbot avatar to identify the requested stored information; and/or (5) providing the identified information to the access user in connection with or during the simulated conversation to facilitate estate or claim handling. The method may include additional, less, or alternate actions, including those discussed elsewhere herein.

For instance, the claim may be a life insurance claim, and the simulated conversation includes the chatbot avatar verbally informing the access user of the insured's intent with respect to the disposition of the insured's personal assets in a voice that mimics that of the insured. The method may include communicating notice to the access user that they have been identified by the insured as an access user entitled to access information upon the occurrence of a triggering event associated with the insured and/or an insurance claim.

The method may include communicating notice to the access user that they have been identified by the insured as an access user entitled to access information upon the occurrence of a triggering event associated with the insured and/or an insurance claim, wherein the occurrence of the triggering event is determined from processor analysis of sensor data received from a mobile device, a smart home controller, wearable device, or smart or autonomous vehicle associated with the insured.

The method may include communicating notice to the access user that they have been identified by the insured as an access user entitled to access information upon the occurrence of a triggering event associated with the insured and/or an insurance claim, wherein the occurrence of the triggering event is determined from processor analysis of home telematics data (including audio and/or digital image data) associated with the insured and/or received from an insured computing device or smart home controller. The claim may be a homeowners insurance claim, a renters insurance claim, or a personal articles insurance claim.

The method may include communicating notice to the access user that they have been identified by the insured as an access user entitled to access information upon the occurrence of a triggering event associated with the insured and/or an insurance claim, wherein the occurrence of the triggering event is determined from processor analysis of vehicle telematics data (including speed, acceleration, corning, braking, location, destination, origin, and/or route information) associated with the insured and/or received from an insured computing device, or smart or autonomous vehicle. The claim may be an auto insurance claim.

Exemplary Computer Systems

In one aspect, a computer system for detecting insurance-related events and handling insurance claims may be provided. The computer system may include one or more local or remote processors, transceivers, servers, and/or sensors. The computer system may include, or be configured to, (1) with a policyholder's permission and affirmative consent, build, via one or more processors and/or associated transceivers, a policyholder profile and/or online policyholder account for the policyholder based upon policyholder input, the policyholder profile including characteristics of the policyholder and policy information; (2) accept, via one or more processors and/or associated transceivers digital, assets uploaded by the policyholder, and associate or otherwise link the digital assets with the policyholder profile; (3) upon the policyholder selecting a beneficiary, contact, via one or more processors and/or associated transceivers, the beneficiary via electronic communication, and then grant the beneficiary electronic access to the policyholder account via a beneficiary app; (4) detect, via one or more processors and/or associated transceivers, an event associated with the policyholder, such as via one or more home, vehicle, wearable, and/or mobile device sensors, or otherwise receiving notification of the event associated with the policyholder, such as via electronic communication with the policyholder's or a beneficiary's mobile device; (5) send, via one or more processors and/or associated transceivers, an electronic notification of the event to the beneficiary; (6) initiate, via one or more processors and/or associated transceivers, a claim based upon the policy and/or the event; and/or (7) display, via one or more processors and/or associated transceivers, the status of the claim via the beneficiary app, or verbally relaying the status of the claim to the beneficiary via the beneficiary app or chatbot, or otherwise allowing, via one or more processors and/or associated transceivers, the beneficiary to track the status of the claim via the beneficiary app to facilitate handling claims in efficient and convenient manner and/or enhance the customer experience. The system may be configured to include additional, less, or alternate functionality, including that discussed elsewhere herein.

For instance, the digital assets may include financial statements, financial account statements, tax information and returns, and/or one or more deeds. Additionally or alternatively, the digital assets may include social media content, telephone voice recordings, and/or emails associated with the policyholder.

The digital assets may be fed into a machine learning algorithm, model, module, or program, via one or more processors and/or associated transceivers, to create a virtual avatar (audible and/or visual (such as a hologram)) with a personality similar to the personality of the policyholder. The machine learning algorithm, model, module, or program may employ supervised or unsupervised machine learning techniques, or other machine learning techniques.

The beneficiary app may allow the beneficiary to have a conversation with the avatar of the policyholder. The digital assets may include one or more passwords to one or more online accounts of the policyholder.

The claim may relate to a life insurance or health insurance policy. Additionally or alternatively, the claim may relate to a homeowners or auto insurance policy. For instance, the claim may relate to an auto insurance policy, and/or vehicle telematics or home sensor data may be analyzed to estimate vehicle damage and repair or replacement costs. Alternatively, the claim may relate to a homeowner's insurance policy, and/or vehicle telematics or home sensor data may be analyzed to estimate home damage and repair or replacement costs.

The digital assets may include monthly, periodic, or otherwise recurring bills, such as telephone, cable, electricity, and water bills, and/or auto or home loan information and statements. The event may be a sickness, illness, or passing away of the policyholder.

The computer system may be configured to allow, via one or more processors and/or associated transceivers, the beneficiary to upload necessary documents, such as a death certificate or doctor's statement, to the online policyholder account. The computer system may be configured to allow, via the one or more processors and/or associated transceivers, the beneficiary to learn the status of the claim via a conversation with a chatbot, and receive answers to questions regarding the claim verbally from the chatbot.

The computer system and/or chatbot avatar may be configured to verbally inform, via the one or more processors and/or associated transceivers, the beneficiary of the actual or likely wishes of the policyholder for various assets via a conversation with the avatar of the policyholder. The computer system and/or chatbot avatar, may be configured to guide, via the one or more processors and/or associated transceivers, the policyholder thru the process of creating a will and/or identifying assets to be transferred to various beneficiaries via a chatbot. The will may provide for long-term management of the policyholder's social media accounts and digital assets, including digital images.

The computer system may be configured to pose, via a chatbot, posing several questions to the policyholder to build a baseline personality for the avatar of the policyholder.

The event may be a vehicle event (e.g., vehicle collision associated with a vehicle covered by an auto insurance policy), and the event and/or vehicle damage may be initially or otherwise detected by one or more vehicle-mounted sensors or mobile device sensors. Additionally or alternatively, the event may be a vehicle event (e.g., vehicle collision associated with a vehicle covered by an auto insurance policy), and the event and/or vehicle damage may be initially or otherwise detected by analyzing vehicle telematics data generated by one or more vehicle-mounted sensors or mobile device sensors, or home sensor (and image) data generated by one or more home-mounted sensors (including cameras).

The event may be a home event (e.g., damage to a home covered by a homeowners insurance policy, or an apartment or condo covered by a policy, or personal belongings damaged that are covered by a personal articles policy), and damage to a home, apartment, condo, and/or personal belongings may be initially or otherwise detected via one or more home-mounted sensors, vehicle-mounted sensors, and/or mobile device sensors.

The event may be a medical event associated with the policyholder and covered by the policy, and the medical event may be initially or otherwise detected by one or more home-mounted sensors, vehicle-mounted sensors, mobile device sensors, smart glasses, smart watches, and/or wearable sensors.

In another aspect, a computer system for estate handling or claim handing via a chatbot avatar having the personality and/or voice mimicking that of an insured may be provided. The computer system may include one or more local or remote processors, transceivers, servers, and/or sensors configured to: (1) receive and/or store personal and/or financial information received from an insured (or first or storage user); (2) generate a chatbot avatar for the insured based upon the personal information received from the insured; (3) receive a request from an access user (or second user) to access the stored information; (4) communicate with the access user by a simulated conversation with the insured via the chatbot avatar to identify the requested stored information; and/or (5) provide the identified information to the access user in connection with or during the simulated conversation to facilitate estate or claim handling. The computer system may include additional, less, or alternate functionality, including that discussed elsewhere herein.

For instance, the claim may be a life insurance claim, and the simulated conversation may include the chatbot avatar verbally informing the access user of the insured's intent with respect to the disposition of the insured's personal assets in a voice that mimics that of the insured.

The computer system may be further configured to communicate notice to the access user that they have been identified by the insured as an access user entitled to access information upon the occurrence of a triggering event associated with the insured and/or an insurance claim.

The computer system may be further configured to communicate notice to the access user that they have been identified by the insured as an access user entitled to access information upon the occurrence of a triggering event associated with the insured and/or an insurance claim, wherein the occurrence of the triggering event is determined from processor analysis of sensor data received from a mobile device, a smart home controller, wearable device, or smart or autonomous vehicle associated with the insured.

The computer system may be further configured to communicate notice to the access user that they have been identified by the insured as an access user entitled to access information upon the occurrence of a triggering event associated with the insured and/or an insurance claim, wherein the occurrence of the triggering event is determined from processor analysis of home telematics data (including audio and digital image data) associated with the insured and/or received from an insured computing device or smart home controller. The claim may be a homeowners insurance claim, renters insurance claim, or a personal articles insurance claim.

The computer system may be configured to communicate notice to the access user that they have been identified by the insured as an access user entitled to access information upon the occurrence of a triggering event associated with the insured and/or an insurance claim, wherein the occurrence of the triggering event is determined from processor analysis of vehicle telematics data (including speed, acceleration, corning, braking, location, destination, origin, and/or route information) associated with the insured and/or received from an insured computing device, or smart or autonomous vehicle. The claim may be an auto insurance claim.

In one aspect, an exemplary computer system to facilitate estate handling may be provided. The computer system may comprise one or more local or remote processors, transceivers, servers and/or sensors. The computer system configured to: (1) store information of a first user; (2) receive a request from a second user to access the stored information; (3) communicate with the second user by a simulated conversation with the first user to identify the requested stored information; and (4) provide the identified information to the second user in connection with the simulated conversation.

Machine Learning & Other Matters

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on mobile computing devices, or associated with smart infrastructure or remote servers), and/or via computer executable instructions stored on non-transitory computer-readable media or medium.

In some embodiments, a customer support platform computing device is configured to implement machine learning, such that the customer support platform computing device "learns" to analyze, organize, and/or process data without being explicitly programmed. Machine learning may be implemented through machine learning methods and algorithms ("ML methods and algorithms"). In an exemplary embodiment, a machine learning module ("ML module") is configured to implement ML methods and algorithms. In some embodiments, ML methods and algorithms are applied to data inputs and generate machine learning outputs ("ML outputs"). Data inputs may include but are not limited to: user or policyholder data, beneficiary data, sensor data, policy data, social media data, digital asset data, financial data, electronic or voice communication data, email and text data, and/or other data types, including those discussed elsewhere herein. ML outputs may include but are not limited to: user or policyholder data, beneficiary data, sensor data, policy data, social media data, digital asset data, financial data, electronic or voice communication data, email and text data, and/or other data types, including those discussed elsewhere herein. In some embodiments, data inputs may include certain ML outputs.

In some embodiments, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, combined learning, reinforced learning, dimensionality reduction, and support vector machines. In various embodiments, the implemented ML methods and algorithms are directed toward at least one of a plurality of categorizations of machine learning, such as supervised learning, unsupervised learning, and reinforcement learning.

In one embodiment, the ML module employs supervised learning, which involves identifying patterns in existing data to make predictions about subsequently received data. Specifically, the ML module is "trained" using training data, which includes example inputs and associated example outputs. Based upon the training data, the ML module may generate a predictive function which maps outputs to inputs and may utilize the predictive function to generate ML outputs based upon data inputs. The example inputs and example outputs of the training data may include any of the data inputs or ML outputs described above. For example, a ML module may receive training data comprising user or policyholder data, beneficiary data, sensor data, policy data, social media data, digital asset data, financial data, electronic or voice communication data, email and text data, and/or other data types, including those discussed elsewhere herein.

In another embodiment, a ML module may employ unsupervised learning, which involves finding meaningful relationships in unorganized data. Unlike supervised learning, unsupervised learning does not involve user-initiated training based upon example inputs with associated outputs. Rather, in unsupervised learning, the ML module may organize unlabeled data according to a relationship determined by at least one ML method/algorithm employed by the ML module. Unorganized data may include any combination of data inputs and/or ML outputs as described above.

For example, a ML module may receive unlabeled data comprising user or policyholder data, beneficiary data, sensor data, policy data, social media data, digital asset data, financial data, electronic or voice communication data, email and text data, and/or other data types, including those discussed elsewhere herein. The ML module may employ an unsupervised learning method such as "clustering" to identify patterns and organize the unlabeled data into meaningful groups.

In yet another embodiment, a ML module may employ reinforcement learning, which involves optimizing outputs based upon feedback from a reward signal. Specifically, the ML module may receive various types of input data to generate one or more ML outputs. Other types of machine learning may also be employed, including deep or combined learning techniques.

Exemplary Digital Asset Service Set Up Method

FIG. 9 depicts an exemplary computer-implemented method 900 to set up or otherwise configure a computer system to provide digital asset storage, management and retrieval functionality and services such as, for example those described in this disclosure. The digital asset storage, management and retrieval functionality and services may be implemented via one or more chatbots or digital assistants, such as a chatbot avatar having a personality and voice similar to that of a policyholder (such as a person covered by a life or health insurance policy) and/or as otherwise discussed herein.

The method 900 may be implemented via one or more local or remote processors, transceivers, sensors (such as wearables, mobile device sensors, vehicle sensors, home sensors, drone sensor, smart glasses, etc.), and/or servers. By way of example, embodiments can be implemented using networks and systems of the types described in connection with FIGS. 2 and 3.

The method 900 may be performed on behalf of a first user, such as a life or other insurance policyholder, which in embodiments may be a user referred to in this disclosure as a "storage" user. For purposes of example, in FIG. 9 and the following description the first user is referred to as the "policyholder." The method 900 may include steps related to a second user, such as a beneficiary of a life or other insurance policyholder, such as family members, which in embodiments may be a user referred to in this disclosure as an "access" user. For purposes of example, in FIG. 9 and the following description the second user is referred to as the "beneficiary."

A third party, such as for example an insurance company that issues the insurance policy to the policyholder (or an entity operating on behalf of the third party), may configure and/or operate components or portions of the network or computer system used to implement the method 900. For purposes of example, in FIG. 9 and the following description the third party is referred to as the "insurance company." The method 900 may include the provision of information storage, management and/or retrieval services by or on behalf of the insurance company, which services are referred to as "Beneficiary App" in FIG. 9.

As shown by step 902, the policyholder may purchase or otherwise obtain a policy from the insurance company. The policy may be purchased through the networked computer system (e.g., on line). In some embodiments, the policy may be purchased through an agent of the insurance company. A record may be established in the computer system in connection with the purchased insurance policy. The record, which may include an account record, may include information about the policyholder, contact information for the policyholder, information about the insurance policy, and/or other information of the types described in this disclosure.

As shown by step 904, the insurance company may invite the policy holder to use the Beneficiary App service. In some embodiments, the invitation can be communicated electronically to the policyholder (e.g., by email, text or voice message). Additionally or alternatively, a written invitation may be provided to the policyholder.

As shown by step 906, the policyholder may enroll in the Beneficiary App service. The enrollment may be in the form of an electronic communication requesting enrollment from the policyholder (e.g., by email or text) that is received by the computer system. In response to a request to enroll, the computer system may create a Beneficiary App record associated with the policyholder. The Beneficiary App record may store information associated with the Beneficiary App services provided to the policyholder.

As shown by step 908, the policyholder may select one or more beneficiaries in connection with the Beneficiary App services. The identity of the selected beneficiary, and contact information for the beneficiary, may be received by the computer system from the policyholder (e.g., electronically), and stored by the computer system (e.g., as part of the policyholder's Beneficiary App record).

As shown by step 910, the policyholder may cause their digital assets and/or information related to the digital assets to be uploaded or stored by the computer system. Non-limiting examples of such digital assets include life, homeowner, medical or vehicle insurance policies and/or information on accounts associated with such insurance policies. Embodiments may include other digital assets described in this disclosure.

In connection with step 910, personal information about the policyholder that can be used to develop a virtual personality of the policyholder or virtual model of the policyholder (e.g., as described in this disclosure) that may be received and stored by the computer system. Such personal information can be received from the policyholder and may be used to create an audible and/or visual (hologram) virtual likeness of the policyholder. The personal information may be in various formats, such as pictures, images, video, and/or audible recordings of the policyholder. Other formats may also be collected, such as social media posts, emails, texts, or other correspondence.

Additionally or alternatively, the policyholder can identify accounts or other sources of such personal information, and the computer system may be configured to collect the personal information from the identified accounts. As noted above, non-limiting examples of such personal information and accounts with such information include voice recordings, images, videos, emails, texts, answers to baseline questions or social media accounts. A chatbot component of the computer system may be configured with the information collected by this step 910 as described in this disclosure.

As shown by step 912, the beneficiary selected by the policyholder receives a notification that they have the opportunity to use the Beneficiary App service. In some embodiments, the notification may be an invitation to the Beneficiary App service. The invitation or other notification may be provided to the beneficiary by the computer system electronically (e.g., by email or text). In some embodiments, the invitation or notification may include information about the source of an app, such as a link, that the beneficiary can use in connection with the Beneficiary App service. The beneficiary may download the app (i.e., the "beneficiary app") onto their communication device (e.g., a computer or mobile device).

As shown at step 914, the beneficiary may enroll in the Beneficiary App service as the policyholder's beneficiary. In some embodiments, the beneficiary may communicate with the computer system through the beneficiary app to provide information for the enrollment process (e.g., contact information). The computer system may provide instructions and/or prompts to the beneficiary in connection with the enrollment process. In certain embodiments, the beneficiary may enroll in the Beneficiary App service though an interactive website provided by the computer system.

In one aspect, an exemplary computer-implemented method to set up or otherwise configure a computer system to provide digital asset storage, management and/or retrieval services on behalf of a user such as an insurance policyholder may be provided. The method may include: (1) with a policyholder's permission, via one or more processors and/or associated transceivers, enrolling the policyholder in a digital asset storage, management and/or retrieval service, wherein enrolling the policyholder optionally includes establishing an account record associated with the policyholder; (2) receiving from the policyholder and/or a beneficiary, via one or more processors and/or transceivers, information about the beneficiary; (3) accepting and storing, via one or more processors and/or associated transceivers, digital assets associated with the policyholder; (4) sending, via one or more processors and/or associated transceivers, a notification to the beneficiary informing the beneficiary of the opportunity to use the digital asset service; (5) receiving from the beneficiary, via one or more processors and/or transceivers, a request to enroll in the digital asset service; (6) enrolling the beneficiary as the policyholder's beneficiary in the digital asset service, wherein enrolling the beneficiary optionally includes storing information associated with the beneficiary in an account record associated with the policyholder; and/or (7) sending to the beneficiary, via one or more processors and/or transceivers, information about a beneficiary app that the beneficiary can download onto a communication device and use in connection with the digital asset services.

The method may further include storing information representative of a virtual personality of the policyholder or a virtual model of the policyholder based upon the digital assets. The digital assets may be fed into a machine learning algorithm, model, module or program, via one or more processors and/or associated transceivers, to create a virtual avatar with a personality similar to the personality of the policyholder. After which, the beneficiary app may allow the beneficiary to have a conversation with the avatar of the policyholder. The method may include additional, less, or alternate actions, including those discussed elsewhere herein.

For instance, the method may further include receiving from the policyholder, via one or more processors and/or associated transceivers, a request to enroll in the digital asset service. In some embodiments, the method may further include sending to the policyholder, via one or more processors and/or associated transceivers, an invitation to enroll in the digital asset service.

In certain embodiments, the insurance policy includes one or more of a life insurance policy, a homeowner or renter insurance policy, a vehicle insurance policy or a medical insurance policy.

In one aspect, an exemplary computer system for providing digital asset storage, management and/or retrieval services in connection with insurance policies may be provided. The computer system may comprise one or more local or remote processors, transceivers, servers and/or sensors. The computer system may be configured to: (1) with a policyholder's permission, via one or more processors and/or associated transceivers, enroll the policyholder in a digital asset storage, management and/or retrieval service, wherein enrolling the policyholder optionally includes establishing an account record associated with the policyholder; (2) receive from the policyholder, via one or more processors and/or transceivers, information about a beneficiary; (3) accept and store, via one or more processors and/or associated transceivers, digital assets associated with the policyholder; (4) send, via one or more processors and/or associated transceivers, a notification to the beneficiary informing the beneficiary of the opportunity to use the digital asset service; (5) receive from the beneficiary, via one or more processors and/or transceivers, a request to enroll in the digital asset service; (6) enroll the beneficiary as the policyholder's beneficiary in the digital asset service, wherein enrolling the beneficiary optionally includes storing information associated with the beneficiary in an account record associated with the policyholder; and (7) send to the beneficiary, via one or more processors and/or transceivers, information about a beneficiary app that the beneficiary can download onto a communication device and use in connection with the digital asset services.

Exemplary Digital Asset Service Method

FIGS. 10A and 10B depict an exemplary computer-implemented method 1000 to operate a computer system to provide digital asset storage, management and retrieval functionality and services, such as for example those described in this disclosure. The digital asset storage, management and retrieval functionality and services may be implemented via one or more chatbots or digital assistants, such as a chatbot avatar having a personality and voice similar to that of a policyholder (such as a person covered by a life or health insurance policy) and/or as otherwise discussed herein.

In some embodiments, the method 1000 may be operated on a computer system set up or configured in accordance with method 900 described above in connection with FIG. 9. The method may be implemented via one or more local or remote processors, transceivers, sensors (such as wearables, mobile device sensors, vehicle sensors, home sensors, drone sensor, etc.), and/or servers. By way of example, embodiments may be implemented using networks and systems of the types described in connection with FIGS. 2 and 3.

The method 1000 may be performed on behalf of a first user, such as a life or other insurance policyholder, which in embodiments may be a user referred to in this disclosure as a "storage" user. For purposes of example, in FIGS. 10A and 10B and the following description, the first user is referred to as the "policyholder."

The method may include steps related to a second user, such as a beneficiary of a life or other insurance policyholder, which in embodiments may be a user referred to in this disclosure as an "access" user. For purposes of example, in FIGS. 10A and 10B and the following description the second user is referred to as the "beneficiary."

A third party, such as for example an insurance company that issues the insurance policy to the policyholder (or an entity on behalf of the third party), may configure and/or operate components or portions of the network or computer system used to implement the method 1000. For purposes of example, in FIGS. 10A and 10B and the following description, the third party is referred to as the "insurance company." The method 1000 may include the provision of information storage, management and/or retrieval services provided by or on behalf of the insurance company, which services are referred to as "Beneficiary App."

As shown by step 1002, a triggering event related to the insurance policy occurs with respect to the policyholder. In connection with a life insurance policyholder, for example, the triggering event may be the passing away of the policyholder. In connection with a homeowner or renter insurance policy, the triggering event may, for example, be a weather-related damage event or a theft from the property. In connection with a vehicle insurance policy, the triggering event may, for example, be an accident involving the vehicle. In connection with a medical or health insurance policy, for example, the triggering event may be an illness diagnosis, hospital admittance, or doctor appointment.

As shown by step 1004, the beneficiary may initiate a claim on the policyholder's insurance policy based upon the triggering event. For example, the beneficiary may initiate a claim on a life insurance policy in situations involving a policyholder's passing. In the illustrated embodiment, the beneficiary may initiate the claim by sending a claim request though the use of the beneficiary app on their communication device.

As shown by step 1006, the insurance company may receive notice of the triggering event. In the illustrated embodiments, the notice may be received from the beneficiary by communications through the beneficiary app. In other embodiments, the insurance company may receive notice of the triggering event by other methods. For example, the beneficiary may communicate notice of the triggering event to the insurance company through the website associated with the digital asset service.

In some embodiments, the insurance company may receive notice of the triggering event from sources other than the beneficiary. For example, the insurance company may receive notice by monitoring public records, such as published obituaries. Monitoring of this type may be done electronically by the computer system, or manually by persons on behalf of the insurance company. Additionally or alternatively, information representative of the triggering events may be received from sensors, monitoring or other devices as described in this disclosure.

As shown by step 1008, the insurance company may communicate with the beneficiary regarding the insurance claim through the beneficiary app. In the illustrated embodiment, for example, the insurance company notifies the beneficiary of requirements or other appropriate actions the beneficiary may take to submit the claim in a form suitable for processing and payment. Such requirements may include, for example, information required by the insurance company to process and pay the claim.

As shown by step 1010, the beneficiary may submit information regarding the claim to the insurance company through the beneficiary app. In embodiments, the information provided by the beneficiary may include information requested by the insurance company.

As shown by step 1012, the insurance company receives and processes the information submitted by the beneficiary in connection with the claim. Such processing can include, for example, confirming the nature of the triggering event, and/or determining whether the insurance company has received sufficient information to complete the processing and approve payment on the claim.

As shown by steps 1014 and 1016, the insurance company may process and pay the claim when it has received sufficient information related to the claim and/or completed associated claim approval processes.

As shown by steps 1018, 1020, 1022 and 1024, the beneficiary may communicate with the insurance company regarding the claim through the use of the beneficiary app. The beneficiary may also access the policyholder's stored digital assets through the use of the beneficiary app. The beneficiary's access to such claim-related information and digital assets through the beneficiary app may be controlled by the insurance company so that the beneficiary may access the information only under authorized conditions.

As shown by step 1018, for example, the insurance company may "unlock" and permit access to the claim-related information and digital assets through the beneficiary app after confirming the triggering event, such as the passing of the policyholder. Additionally or alternatively, other conditions such as authentication of the beneficiary may be enforced before the beneficiary is allowed to access the policyholder's stored digital assets and/or communicate with the insurance company about the claim using the beneficiary app.

As shown by step 1020, the beneficiary may use the beneficiary app to monitor the status of the claim process. In connection with this use of the beneficiary app, for example, the beneficiary may access or receive information describing claim process steps that have been completed and/or claim process steps that are uncompleted. Timing information such as anticipated dates for completion of the steps may be provided to the beneficiary. Through use of the beneficiary app the beneficiary may also receive notice of information the beneficiary may provide to the insurance company (e.g., outstanding information that is required) to facilitate completion of the claim process.

As shown by step 1022, the beneficiary may receive benefits pursuant to the claim and/or policy (e.g., an electronic payment) through the beneficiary app. The claim may be accompanied by instructions or associated information from the policyholder. In some embodiments, the instructions or other accompanying information may be personalized from the stored digital assets of the policyholder and personalized by the policyholder. For example, the beneficiary may receive information about the policyholder's intentions regarding the claim and payment, as well as the policyholder's intentions for various digital assets, financial assets, and/or other assets or personal belongings.

As shown by step 1024, by the communications with the policyholder and/or insurance company through the beneficiary app the beneficiary may receive information regarding long-term management of the policyholder's digital assets. For example, the beneficiary may receive information for management of the policyholder's social media accounts, including digital images, or the transfer of the digital assets to other parties (e.g., other beneficiaries).

The communications using the beneficiary app (e.g., per steps 1020, 1022 and 1024) may be in the form of chatbot conversations between the beneficiary and the chatbot avatar of the policyholder (e.g., by text or speech). During these communications the responses provided by the insurance company to the beneficiary may simulate personal characteristics (e.g., sounds, speech patterns, personal and anecdotal knowledge and looks or appearance) of the policyholder (e.g., are provided using a virtual model of the policyholder's personality). The beneficiary may feel that they are conversing directly with the policyholder. In other words, the computer system may be programmed to be the avatar or doppelganger of the policyholder as described in this disclosure. Certain embodiments may include features of the chatbot and avatar described in this disclosure.

In some embodiments, a beneficiary may use the beneficiary app to obtain personalized assistance and/or information about a life insurance policy claim. For example, the beneficiary may want to know the status of the claim, and the policyholder's intentions for the use of the death benefit. In a scenario of this type, the following text is an example of a chatbot conversation that the beneficiary may have with the insurance company using the beneficiary app (through a virtual personal assistant ("Alexa").

Beneficiary: "Hey Alexa, when will I receive the claim from John's life insurance policy?"

Alexa: "Let me check."

Alexa: [After checking insurance company records and the policyholder's digital assets based upon beneficiary app communication.] "You're about 90% finished. Once the insurance company reviews a few documents you'll receive the payment. It should be deposited next week."

Beneficiary: "That's great. I'm worried about what to do with so much money. What would John have wanted?"

Alexa: [After checking insurance company records and the policyholder's digital assets based upon beneficiary app communication.] "John's will said that he would like to entrust assets to send Johnnie to college. Would you like to speak to an agent about college savings options?"

Beneficiary: "Yes please."

Alexa: [After checking insurance company records and the policyholder's digital assets based upon beneficiary app communication.] "Check your beneficiary app. The insurance company just sent you a link to an agent's website and contact information." [Additionally or alternatively, a call can be placed to the agent.]

In one aspect, an exemplary computer-implemented method of providing digital asset storage, management and/or retrieval services in connection with insurance policies may be provided. The method may be implemented via one or more local or remote processors, transceivers, servers and/or sensors. The method may include: (1) providing to a beneficiary via a beneficiary app, via one or more processors and/or transceivers and electronic communication, notice of information requested for submission of a claim on an insurance policy; (2) receiving from the beneficiary via the beneficiary app, via one or more processors and/or transceivers via electronic communication, information supporting the claim on the insurance policy; (3) processing, via one or more processors and/or transceivers, the claim on the insurance policy based upon the received information supporting the claim on the insurance policy, wherein the processing includes accessing stored digital assets of the policyholder; (4) receiving from the beneficiary via the beneficiary app, via one or more processors and/or transceivers via electronic communication, requests for information regarding the claim on the insurance policy; and/or (5) displaying via the beneficiary app, via one or more processors and/or associated transceivers, the status of the claim, or verbally relaying the status of the claim to the beneficiary via the beneficiary app or chatbot, or otherwise allowing, via one or more processors and/or associated transceivers, the beneficiary to track the status of the claim via the beneficiary app to facilitate handling claims in efficient and convenient manner and/or enhance the customer experience. The method may include additional, less, or alternate actions, including those discussed elsewhere herein.

For instance, the computer-implemented method may include receiving from the beneficiary via the beneficiary app, via one or more processors and/or transceivers via electronic communication, a request to initiate the claim on the insurance policy. The computer-implemented method may include paying the claim on the insurance policy to the beneficiary via the beneficiary app, via one or more processors and/or associated transceivers via electronic communication.

In another aspect, the computer implemented method may include via one or more processors and/or associated transceivers, allowing the beneficiary to have a conversation with a chatbot avatar of the policy holder by one or both of text or speech. For example, the computer implemented method may comprise via one or more processors and/or associated transceivers, allowing the beneficiary to learn the status of the claim via a conversation with a chatbot, and to receive answers to questions regarding the claim by one or both of text or speech. Additionally or alternatively, the computer implemented method may include, via one or more processors and/or associated transceivers, informing the beneficiary of the actual or likely wishes of the policyholder via a conversation with the avatar of the policyholder, by one or both of text or speech. Additionally or alternatively, the computer implemented method may include, via one or more processors and/or associated transceivers, allowing the beneficiary to receive personalized instructions from the policyholder via access to the stored digital assets of the policyholder.

In another aspect, the computer implemented method may include via one or more processors and/or associated transceivers, allowing the beneficiary to manage the stored digital assets of the policyholder, including online assets, social media context, and digital images and recordings.

In one aspect, an exemplary computer system for providing digital asset storage, management and/or retrieval services in connection with insurance policies is disclosed. The computer system my comprise one or more local or remote processors, transceivers, servers and/or sensors. The computer system may be configured to: (1) provide to a beneficiary via a beneficiary app, notice of information requested for submission of a claim on an insurance policy; (2) receive from the beneficiary via the beneficiary app, information supporting the claim on the insurance policy; (3) process the claim on the insurance policy based upon the received information supporting the claim on the insurance policy, including accessing stored digital assets of the policyholder; (4) receive from the beneficiary via the beneficiary app, requests for information regarding the claim on the insurance policy; and (5) allow, via the beneficiary app, the beneficiary to track the status of the claim to facilitate handling claims.

ADDITIONAL CONSIDERATIONS

With the foregoing, users, policyholders, and beneficiaries may opt-in or register to a customer support platform program or other type of program. After the users, policyholders, and/or beneficiaries give their affirmative consent or permission, a customer support platform remote server may collect data from the mobile devices, user computing devices, smart home controllers, wearables, smart vehicles, autonomous or semi-autonomous vehicles, smart infrastructure, smart buildings, smart aerial devices (e.g., drones), home-mounted sensors, vehicle-mounted sensors, mobile device sensors, and/or other smart devices, such as with the permission or affirmative consent of the users, policyholders, and/or beneficiaries. The data collected may be related to user activities and/or electronic communications, such as social media or email communications, for instance.

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a sever computer. In a further embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes.

In some embodiments, registration of users for the customer support platform includes opt-in informed consent of users to data usage by the smart home devices, wearable devices, mobile devices, autonomous vehicles, and/or smart vehicles consistent with consumer protection laws and privacy regulations. In some embodiments, the user data, and/or other collected data may be anonymized and/or aggregated prior to receipt such that no personally identifiable information (PII) is received. In other embodiments, the system may be configured to receive user data and/or other collected data that is not yet anonymized and/or aggregated, and thus may be configured to anonymize and aggregate the data. In such embodiments, any PII received by the system is received and processed in an encrypted format, or is received with the consent of the individual with which the PII is associated. In situations in which the systems discussed herein collect personal information about individuals, or may make use of such personal information, the individuals may be provided with an opportunity to control whether such information is collected or to control whether and/or how such information is used. In addition, certain data may be processed in one or more ways before it is stored or used, so that personally identifiable information is removed.

As used herein, an element or step recited in the singular and proceeded with the word "a" or "an" should be understood as not excluding plural elements or steps, unless such exclusion is explicitly recited. Furthermore, references to "exemplary embodiment" or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method of setting up a computer system to provide digital asset storage, management and/or retrieval services, the method comprising:

with a storage user's permission, via one or more processors and/or transceivers, enrolling the storage user in a digital asset storage, management and/or retrieval service, wherein enrolling the storage user optionally includes establishing an account record associated with the storage user;

receiving from the storage user, via the one or more processors and/or transceivers, information about one or more access users associated with the storage user;

accepting and storing, via the one or more processors and/or transceivers, digital assets associated with the storage user, wherein the digital assets relate to one or more of a life insurance policy, a homeowner or renter insurance policy, a vehicle insurance policy and a medical insurance policy;

sending, via the one or more processors and/or transceivers, a notification to one or more of the access users informing the one or more access users of an opportunity to use a digital asset service;

receiving from the one or more access users, via the one or more processors and/or transceivers, a request to enroll in the digital asset service;

enrolling the one or more access users in the digital asset service, wherein enrolling the one or more access users includes storing information associated with the one or more access users in an account record associated with the storage user; and sending to the one or more access users, via the one or more processors and/or transceivers, information about an access user app that the access user can download onto a communication device and use in connection with the digital asset services.

2. The computer-implemented method of claim 1, further comprising receiving from the storage user, via the one or more processors and/or transceivers, a request to enroll in the digital asset service.

3. The computer-implemented method of claim 1, further comprising sending to the storage user, via the one or more processors and/or transceivers, an invitation to enroll in the digital asset service.

4. The computer-implemented method of claim 1, further comprising storing information representative of a virtual personality of the storage user or a virtual model of the storage user based upon the digital assets.

5. The computer-implemented method of claim 1, wherein the digital assets are fed into a machine learning module via the one or more processors and/or transceivers, to create a virtual avatar with a personality similar to the personality of the storage user.

6. The computer-implemented method of claim 5, wherein the access user app allows the access user to have a conversation with the avatar of the storage user.

7. The computer-implemented method of claim 1, wherein receiving from the storage user, via the one or more processors and/or transceivers, information about one or more access users associated with the storage user includes receiving condition information including one or more of (1) limitations on roles of the one or more access users and/or (2) types of information that can be provided to the one or more access users.

8. The computer-implemented method of claim 1, further comprising prompting the storage user to provide the information about an access user and the digital assets.

9. The computer-implemented method of claim 1, wherein the computer-implemented method is offered by a third party to provide services to the storage user and/or the one or more access users.

10. A computer system for providing digital asset storage, management and/or retrieval services, the computer system comprising one or more local or remote processors, transceivers, servers and/or sensors, the computer system configured to:

with a storage user's permission, via the one or more processors and/or transceivers, enroll the storage user in a digital asset storage, management and/or retrieval service, wherein enrolling the storage user optionally includes establishing an account record associated with the storage user;

receive from the storage user, via the one or more processors and/or transceivers, information about one or more access users associated with the sotrage user;

accept and store, via the one or more processors and/or transceivers, digital assets associated with the storage user, wherein the digital assets relate to one or more of a life insurance policy, a homeowner or renter insurance policy, a vehicle insurance policy and a medical insurance policy;

send, via the one or more processors and/or transceivers, a notification to one or more of the one or more access users informing the one or more access users of an opportunity to use a digital asset service;

receive from the one or more access users, via the one or more processors and/or transceivers, a request to enroll in the digital asset service;

enroll the one or more access users in the digital asset service, wherein enrolling the one or more access users includes storing information associated with the one or more access users in an account record associated with the storage user; and send to the one or more access users, via the one or more processors and/or transceivers, information about an access user app that the access user can download onto a communication device and use in connection with the digital asset services.

11. The computer system of claim 10, wherein the computer system is further configured to receive from the storage user, via the one or more processors and/or transceivers, a request to enroll in the digital asset service.

12. The computer system of claim 10, wherein the computer system is further configured to send to the storage user, via the one or more processors and/or transceivers, an invitation to enroll in the digital asset service.

13. The computer system of claim 10, wherein the computer system is further configured to store information representative of a virtual personality of the storage user or a virtual model of the storage user based upon the digital assets.

14. The computer system of claim 10, wherein the computer system is further configured to provide a machine learning module via the one or more processors and/or transceivers, to create a virtual avatar with a personality similar to the personality of the storage user based upon the digital assets.

15. The computer system of claim 14, wherein the access user app is configured to allow the access user to have a conversation with the avatar of the storage user.

16. The computer system of claim 10, wherein receiving from the storage user, via the one or more processors and/or transceivers, information about one or more access users associated with the storage user includes receiving condition information including one or more of (1) limitations on roles of the one or more one or more access users and/or (2) types of information that can be provided to the one or more access users.

17. The computer system of claim 10, wherein the computer system is further configured to prompt the storage user to provide the information about an access user and the digital assets.

18. A non-transitory computer-readable storage device storing instructions that, when executed by one or more processors cause the one or more processors to:

enroll a storage user in a digital asset storage, management and/or retrieval service, wherein enrolling the storage user optionally includes establishing an account record associated with the storage user;

receive, from the storage user, information about one or more access users associated with the storage user;

accept and store digital assets associated with the storage user, wherein the digital assets relate to one or more of a life insurance policy, a homeowner or renter insurance policy, a vehicle insurance policy and a medical insurance policy;

send a notification to one or more of the one or more access users informing the one or more access users of an opportunity to use a digital asset service;

receive from the one or more access users a request to enroll in the digital asset service;

enroll the one or more access users as the storage user's access users in the digital asset service, wherein enrolling the one or more access users includes storing information associated with the one or more access users in an account record associated with the storage user; and send to the one or more access users information about an access user app that the access user can download onto a communication device and use in connection with the digital asset services.

* * * * *